United States Patent
Ross et al.

(10) Patent No.: US 7,108,659 B2
(45) Date of Patent: Sep. 19, 2006

(54) RESPIRATORY ANALYZER FOR EXERCISE USE

(75) Inventors: Lynette Ross, Mountain View, CA (US); Dirk Fengels, Santa Cruz, CA (US); Edwin M. Pearce, Jr., San Francisco, CA (US); James R. Mault, Evergreen, CO (US); Christopher L. Sandys, Evergreen, CO (US); Tom Kilbourn, Saratoga, CA (US)

(73) Assignee: HealtheTech, Inc., Golden, CO (US)

( * ) Notice: Subject to any disclaimer, the term of this patent is extended or adjusted under 35 U.S.C. 154(b) by 40 days.

(21) Appl. No.: 10/631,304

(22) Filed: Jul. 31, 2003
(Under 37 CFR 1.47)

(65) Prior Publication Data

US 2004/0186390 A1    Sep. 23, 2004

(51) Int. Cl.
*A61B 5/08*    (2006.01)
(52) U.S. Cl. .................. 600/529; 600/532; 600/538
(58) Field of Classification Search ........ 600/300–301, 600/529–543; 73/23.3
See application file for complete search history.

(56) References Cited

U.S. PATENT DOCUMENTS

| | | | |
|---|---|---|---|
| 3,725,658 A * | 4/1973 | Stanley et al. ............. | 250/364 |
| 4,368,740 A * | 1/1983 | Binder ..................... | 600/531 |
| 4,444,202 A * | 4/1984 | Rubin et al. ............... | 600/538 |
| 4,631,966 A | 12/1986 | Brugnoli | |
| 4,658,832 A | 4/1987 | Brugnoli | |
| 5,046,491 A * | 9/1991 | Derrick ................. | 128/200.24 |
| 5,060,656 A | 10/1991 | Howard | |
| 5,117,674 A | 6/1992 | Howard | |
| 5,363,857 A | 11/1994 | Howard | |
| 5,419,326 A | 5/1995 | Harnoncourt | |
| 5,503,151 A | 4/1996 | Harnoncourt et al. | |
| 5,517,313 A | 5/1996 | Colvin, Jr. | |
| 5,645,071 A | 7/1997 | Harnoncourt et al. | |
| 5,647,370 A | 7/1997 | Harnoncourt | |
| 5,796,009 A | 8/1998 | Delsing | |
| 5,894,351 A | 4/1999 | Colvin | |
| 5,910,661 A | 6/1999 | Colvin | |
| 5,917,605 A | 6/1999 | Colvin | |
| 6,206,837 B1 | 3/2001 | Brugnoli | |
| 6,304,766 B1 | 10/2001 | Colvin | |
| 6,330,464 B1 | 12/2001 | Colvin et al. | |
| 6,344,360 B1 | 2/2002 | Colvin et al. | |
| 6,379,312 B1 * | 4/2002 | O'Toole .................. | 600/529 |
| 6,402,698 B1 * | 6/2002 | Mault ..................... | 600/532 |
| 6,468,222 B1 | 10/2002 | Mault et al. | |
| 6,544,172 B1 * | 4/2003 | Toeppen-Sprigg .......... | 600/300 |
| 6,790,178 B1 * | 9/2004 | Mault et al. ............. | 600/300 |
| 2003/0023182 A1 | 1/2003 | Mault et al. | |
| 2003/0028120 A1 | 2/2003 | Mault et al. | |
| 2003/0065273 A1 | 4/2003 | Mault et al. | |
| 2003/0065274 A1 | 4/2003 | Mault et al. | |
| 2003/0065275 A1 | 4/2003 | Mault et al. | |
| 2003/0105407 A1 | 6/2003 | Mault et al. | |
| 2004/0199083 A1* | 10/2004 | Mault ...................... | 600/532 |

* cited by examiner

*Primary Examiner*—Robert L. Nasser
*Assistant Examiner*—Patricia C. Mallari
(74) *Attorney, Agent, or Firm*—Cooley Godward LLP

(57) ABSTRACT

A respiratory analyzer comprises a flow module, having a flow tube through which the flow rate of gases is determined using a flow rate meter, and a computation module, in communication with the flow module, operable to determine a flow rate of respired gases. The computation module may also be operable to determine a metabolic rate of the subject.

15 Claims, 25 Drawing Sheets

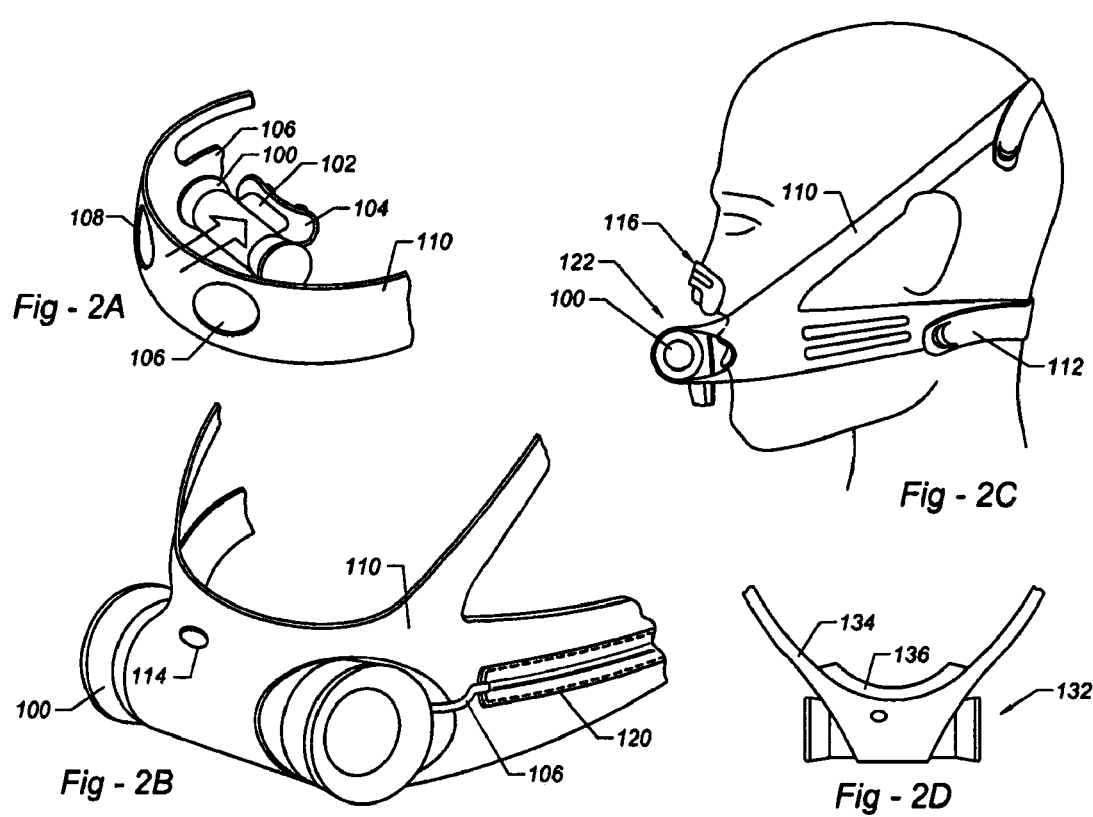

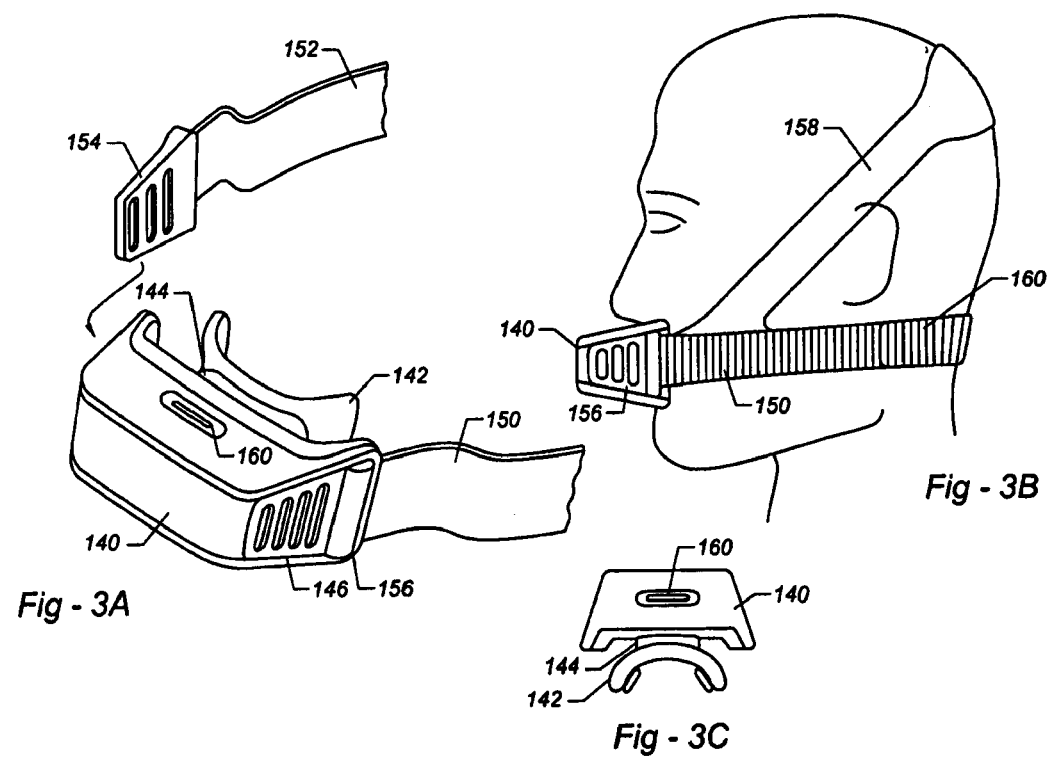

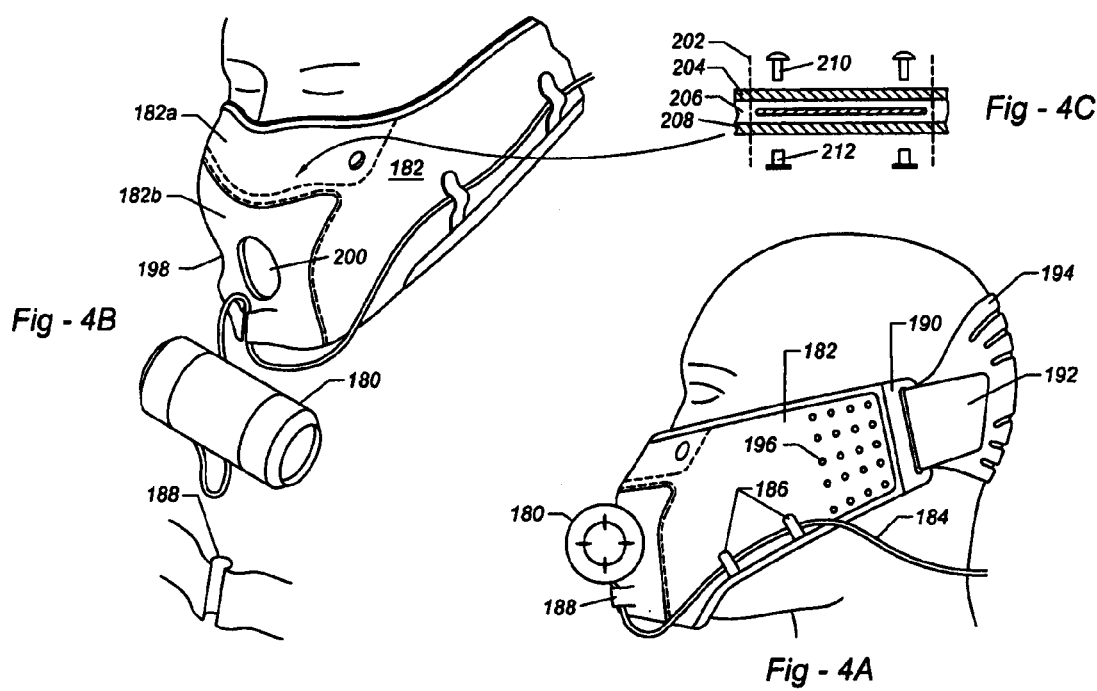

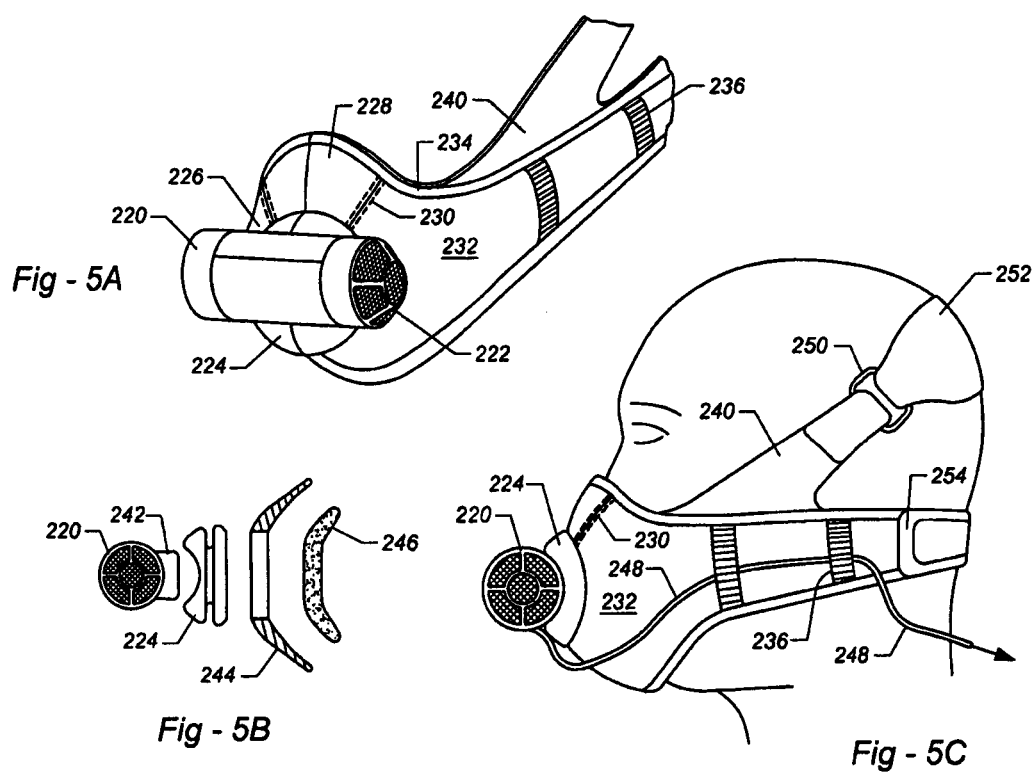

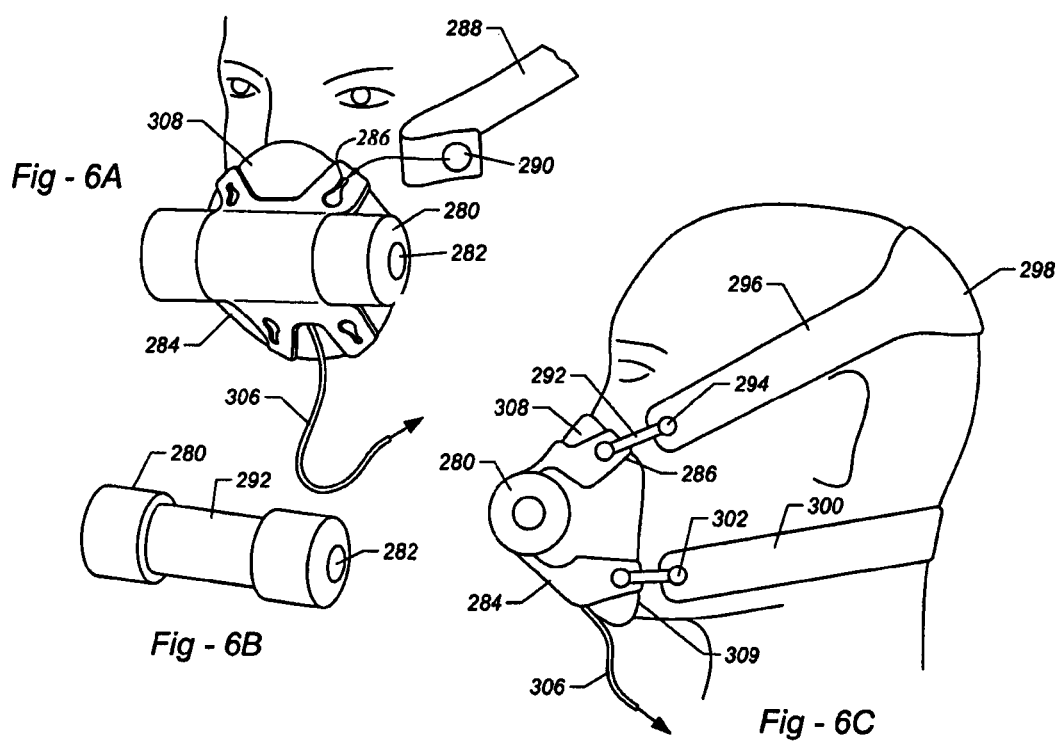

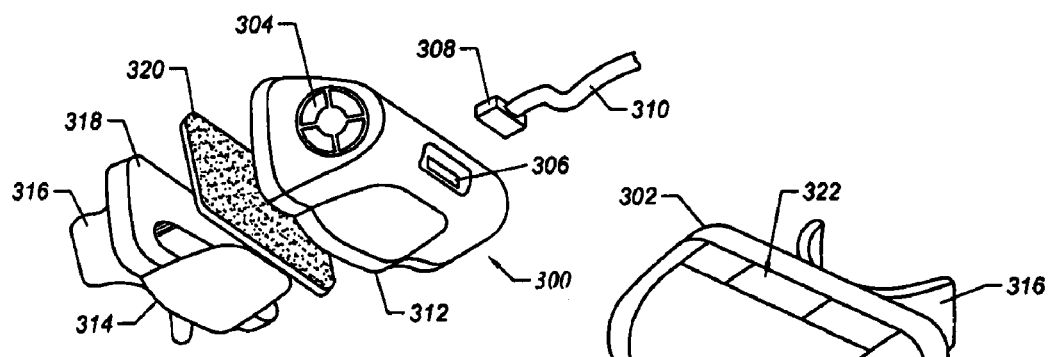
*Fig - 7A*
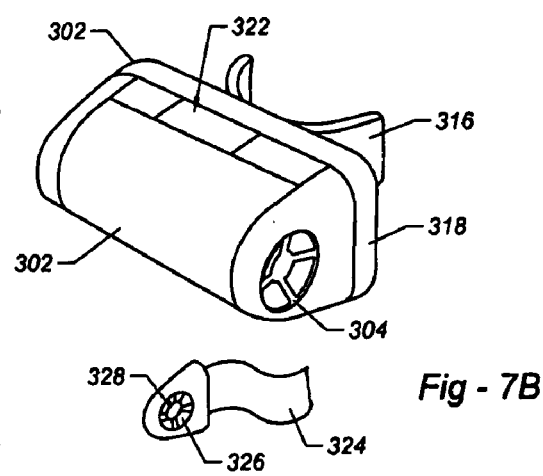
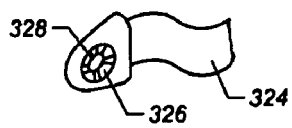
*Fig - 7B*

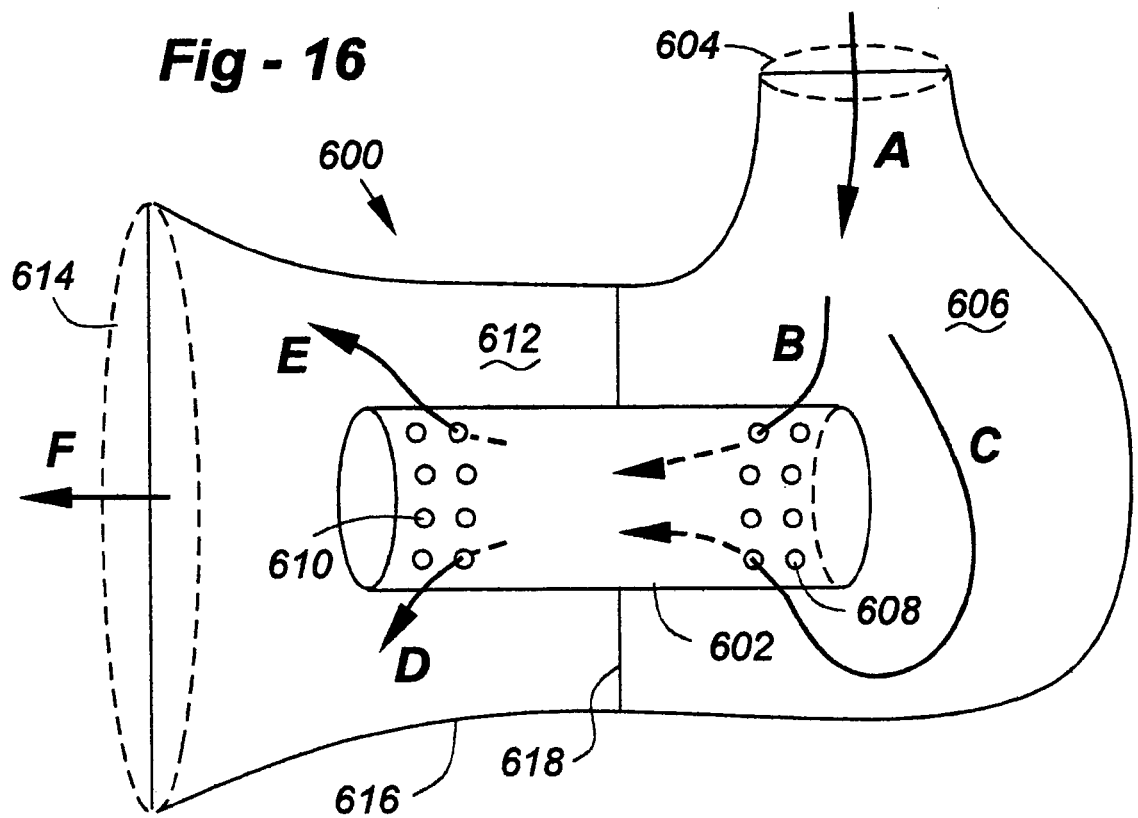
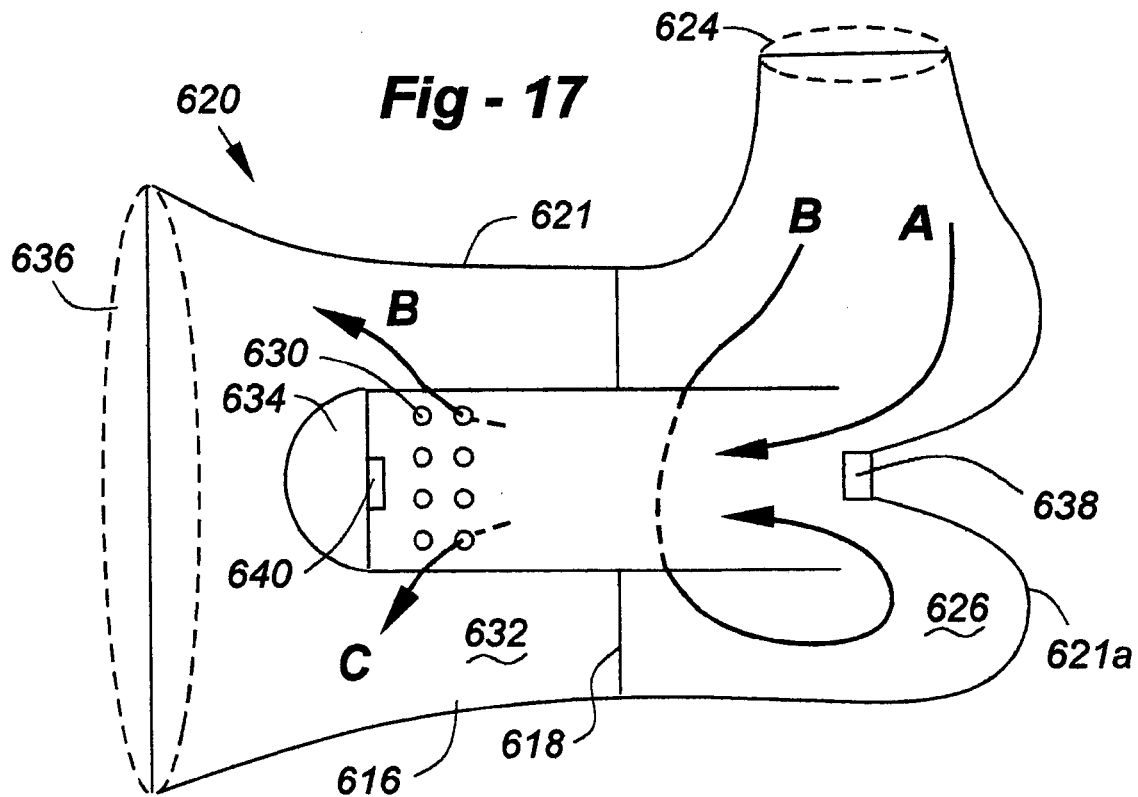

US 7,108,659 B2

RESPIRATORY ANALYZER FOR EXERCISE USE

REFERENCE TO RELATED APPLICATIONS

This application claims the benefit of U.S. Provisional Application Nos. 60/400,265, filed Aug. 1, 2002, and 60/412,155, filed Sep. 19, 2002, the contents of all of which are incorporated herein by reference.

FIELD OF THE INVENTION

This invention relates to respiratory analyzers and metabolic rate measurements, for example to indirect calorimeters.

BACKGROUND OF THE INVENTION

U.S. Pat. No. 6,468,222 to Mault et al. discloses an indirect calorimeter having a flow pathway, through which respired gases pass, a flow meter, and a gas component sensor. Oxygen consumption can be determined for a subject at rest, allowing their resting metabolic rate to be determined.

Ultrasonic transducers can be used to measure flow rates of gases within a flow pathway, for example as described in U.S. Pat. Nos. 5,419,326, 5,503,151, 5,645,071, and 5,647,370 to Hamoncourt, and U.S. Pat. No. 5,796,009 to Delsing.

Oxygen sensors provide a signal correlated with oxygen partial pressure within respired gases. Fluorescent oxygen sensors can be used to determine the oxygen concentration in respired gases, for example as described by Colvin in U.S. Pat. Nos. 6,344,360, 6,330,464, 6,304,766, 5,917,605, 5,910,661, 5,894,351, and 5,517,313.

Respiratory analyzers are described by Brugnoli in U.S. Pat. Nos. 6,206,837, 4,658,832, and 4,631,966. These devices use a turbine flow meter that may be subject to errors due to inertial effects. Indirect calorimeters are also described in U.S. Pat. Nos. 5,060,656, 5,117,674, and 5,363,857, to Howard. These devices use a sampling method to analyze respired gases, which adds to weight, expense, and complexity.

Other respiratory analyzers are described in U.S. patent application Nos. 2003/0065273, 2003/0023182, 2003/0105407, 2003/0028120, 2003/0065274, and 2003/0065275, to Mault and co-inventors.

All U.S. patents and patent applications referred to in this application are incorporated herein by reference. U.S. Provisional Applications Nos. 60/400,265 (filed Aug. 1, 2002), 60/405,850 (filed Aug. 23, 2002), 60/412,155 (filed Sep. 19, 2002), 60/413,505 (filed Sep. 25, 2002), 60/429,252 (filed Nov. 26, 2002), and 60/445,595 (filed Nov. 26, 2002) are incorporated herein by reference.

SUMMARY OF THE INVENTION

A respiratory analyzer according to an embodiment of the present invention comprises a flow module, through which respired gases pass, and a computation module operable to determine a respiratory parameter such as oxygen consumption. The flow module is supported so that a subject breathes through the flow module so that respired gases pass through a flow pathway. The flow module includes a flow rate meter and a gas component sensor. The flow module is in communication with a computation module, which is supported by the body of a subject. The functionality of described computation modules described may also be incorporated into flow modules so as to provide a respiratory analyzer within a unitary device.

Improved configurations of flow paths through a flow module are described which facilitate accurate determination of respiratory parameters, such as oxygen consumption of a subject.

BRIEF DESCRIPTION OF THE DRAWINGS

FIGS. 2A–2D show a respiratory analyzer having a support harness.

FIGS. 3A–3C show a respiratory analyzer having a strap.

FIGS. 4A–4C show an embodiment in which the support harness comprises a flexible sandwich material.

FIGS. 5A–5C show an embodiment of the present invention comprising a mask.

FIGS. 6A–6C show an embodiment in which the flow module is supported by a clamp.

FIGS. 7A and 7B show a configuration of a flow module.

FIGS. 16 and 17 show cross-sections of a flow pathway.

DETAILED DESCRIPTION OF THE INVENTION

A. Respiratory Analyzers

Figure 1A:
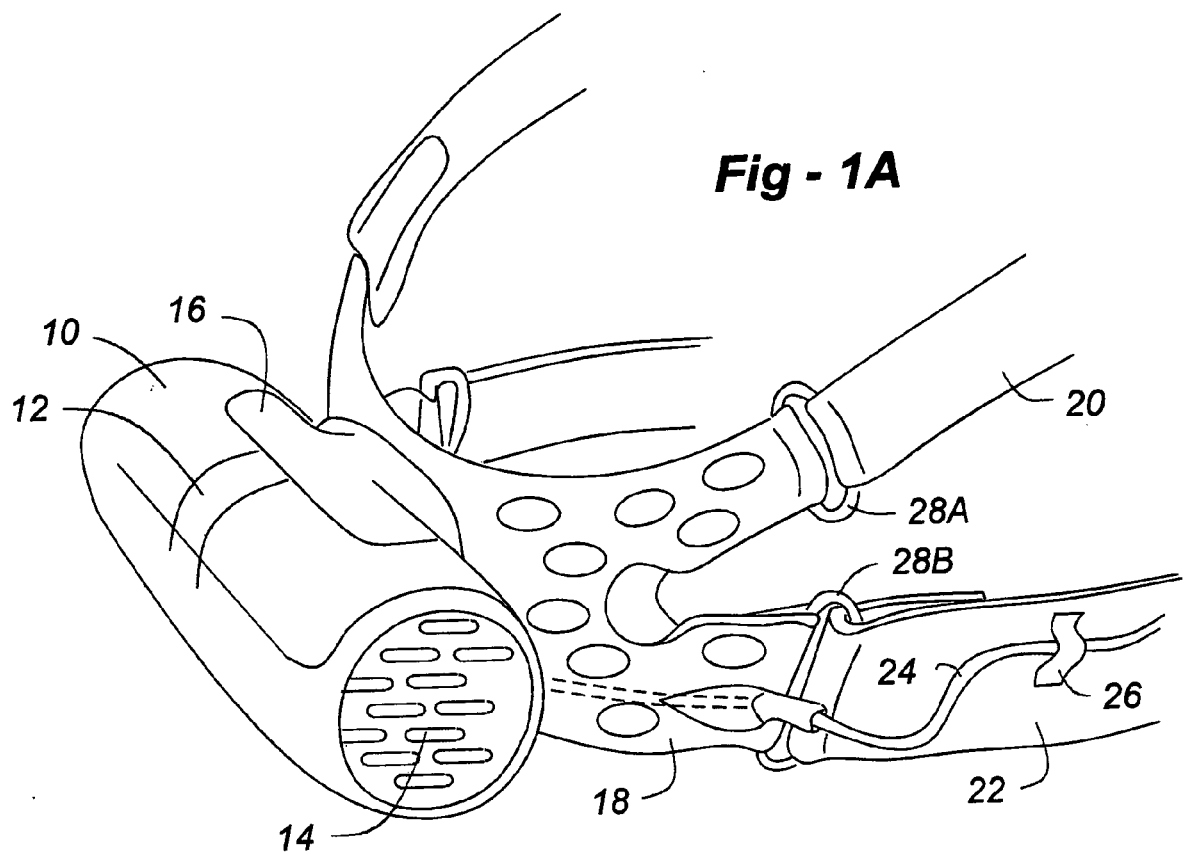
FIGS. 1A–1D show an embodiment of an improved respiratory analyzer.

FIG. 1A show a respiratory analyzer comprising a flow module 10 having a respiratory connector 16 through which the subject breathes. The flow module 10 also has an atmospheric port 14, so that inhaled gases pass through port 14 into the flow module, through a flow pathway enclosed by the housing of the flow module, and further passing through the respiratory connector 16 into the subject's mouth. The flow module comprises an oxygen sensor, covered by window 12, and a flow meter (not shown). The harness includes holes for better ventilation, and may be formed from a transparent polymer.

Support harness 18 supports the flow module so that the respiratory connector is in fluid communication with the subject's mouth. Straps 20 and 22 connect to the support harness 18 using connectors 28a and 28b, the straps passing around the subject's head. The harness contains holes for ventilation.

A cable 24, supported by cable holder 26, connects the flow module with a remote computation module (not shown), which will be discussed in more detail later.

The window is used with fluorescence oxygen sensors to allow the source of excitation radiation, typically a blue light emitting diode, to be viewed by the subject. However, this may degrade performance of the sensor.

In one embodiment, the flow module comprises a flow pathway through which the respired gases pass, a flow meter detecting flow rates of respired gases, and a gas sensor responsive to the partial pressure of one or more components of respired gases. Respired gases include inhaled and/or exhaled gases. In some embodiments, respired gases may include rebreathed gases. For example, the gas sensor may be an oxygen sensor or a carbon dioxide sensor. The example of an oxygen sensor is discussed below.

In one example, the flow module 10 comprises a flow meter and an oxygen sensor. Data signals provided by the oxygen sensor and the flow meter pass through cable 24, held in place by cable holder 26, to a remote computation module (not shown). The cable 24 may be connected to the flow module housing, connect to a conductive path within the flow module, or otherwise provide electrical communication between the sensor and flow meter and the computation module.

Oxygen sensor and flow meter control signals pass from the remote computation module to the flow module through the cable 24. The computation module, discussed in more detail later, provides circuitry adapted to calculate respiratory parameters from signals received from the oxygen sensor and flow meter provided within the flow module, as discussed in more detail later.

As shown in FIG. 1A, the flow pathway of the flow module is in fluid communication with the atmosphere. In other embodiments, the flow pathway can in fluid communication with some other source or sink of respired gases (such as a ventilator, gas cylinder, valve assembly, breathing apparatus, rebreathing apparatus, etc.) through the atmospheric port or other fluid connection.

As shown in FIG. 1A, the person breathes through a mouthpiece. A mask or other device can also be used to help ensure gases respired by the subject pass through the flow module. For example, tubes may be inserted into or over the nostrils and lead respired gas to the flow module.

Figure 1B:
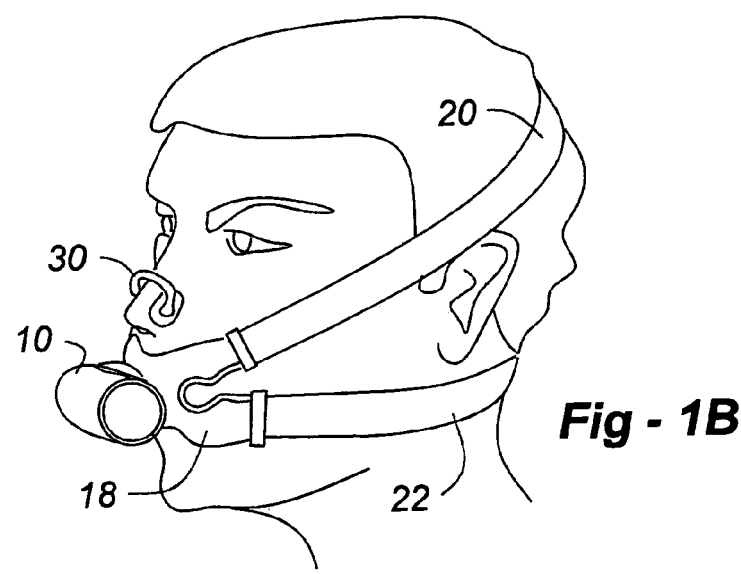

FIG. 1B further shows the flow module 10 supported by the head of a subject using the straps 20 and 22. A separate nose clip 30 is used to help ensure all respired gases pass through the flow module 10.

Figure 1C:
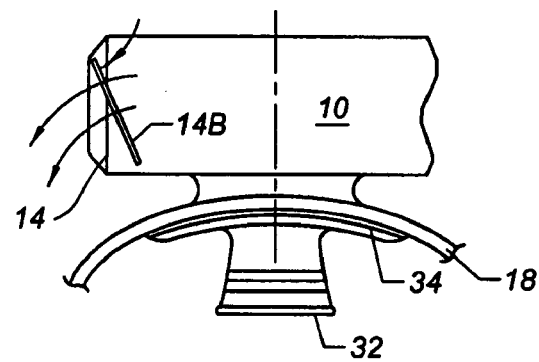

FIG. 1C shows a top view of the respiratory analyzer comprising the flow module 10. A grille 14 covers the atmospheric port. FIG. 1C also shows an alternative configuration of the atmospheric port, in which a grille 14b covering the atmospheric port is angled with respect to the flow module, for wind-breaking. FIG. 1C also shows the respiratory connector including mouthpiece 32 and filler module 34.

Figure 1D:
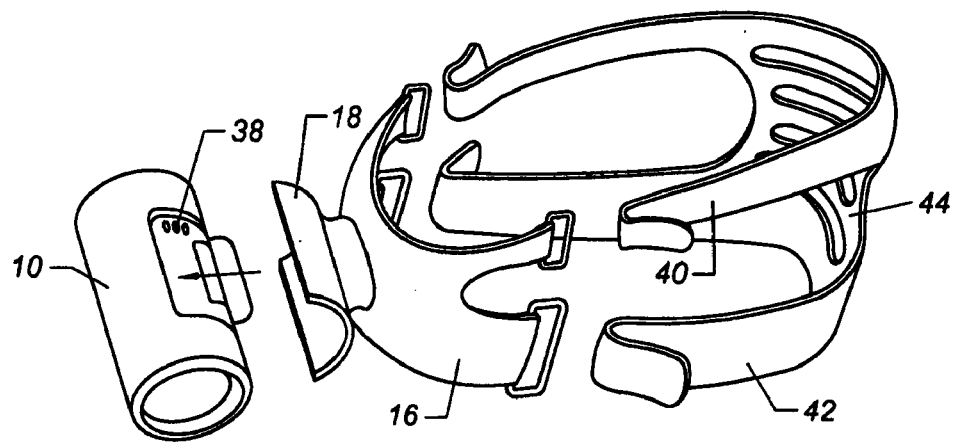

FIG. 1D further illustrates a possible assembly of the system. The flow module 10 is shown with the respiratory connector 16 detached. Straps 40 and 42 are used to support the support harness 18, the straps being connected by webbing 44. The flow tube also has a metal contact 38, for data communication.

Figure 1E:
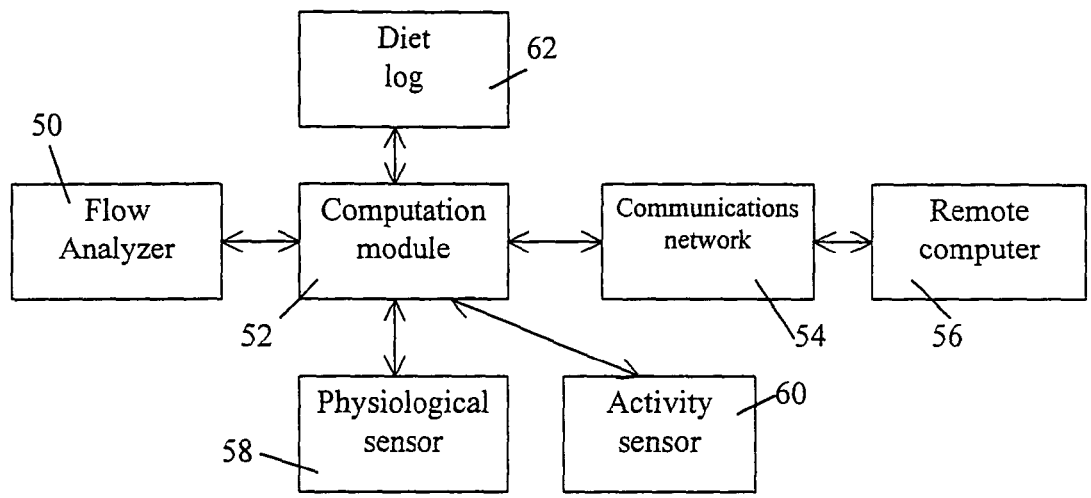
FIGS. 1E and 1F show schematics of respiratory analyzers.

FIG. 1E is a schematic of a respiratory analyzer. The system comprises a flow module 50 in communication with a computation module 52. The computation module also (optionally) receives data from physiological sensor 58, activity monitor 60, and diet log recording 62, and data may be transmitted over communications network 54 for storage, analysis, or review at remote computer 56. The remote computer may provide a database for storage of respiratory parameters, metabolic rate, or other physiological parameters.

Figure 1F:
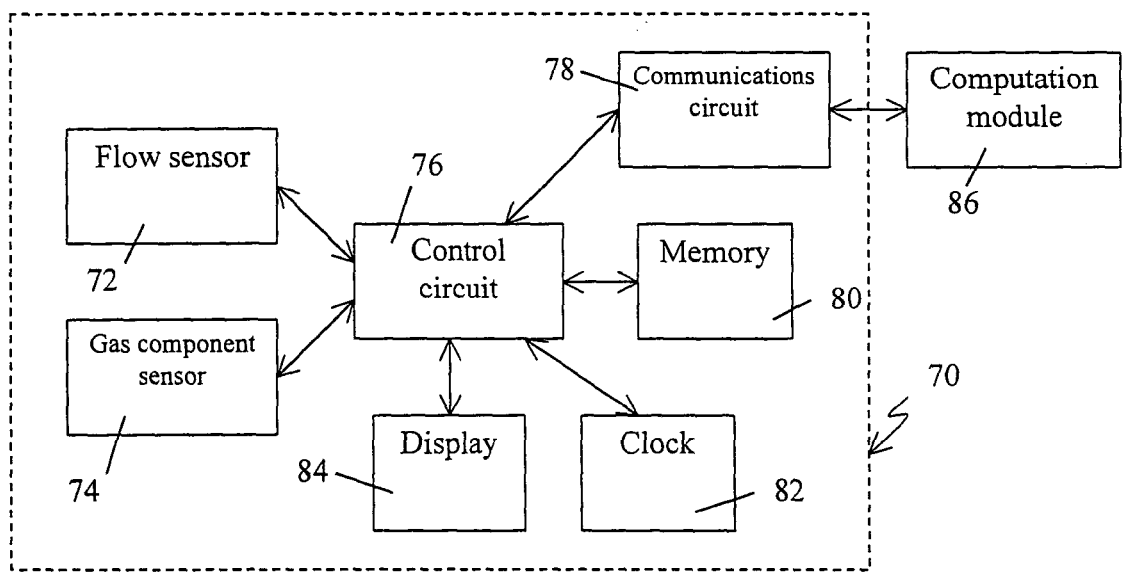

FIG. 1F shows a possible schematic of the electronic circuit shown generally at 70 within an embodiment of a flow module. The flow module comprises a flow meter 72, gas component sensor 74, control circuit 76 adapted to control the measurement devices and receive data from them, memory 80, clock 82, display 84, and a communications circuit 78 adapted to transmit data to a computation module 88. The control circuit may comprise a processor and/or one or more application specific integrated circuits (ASICs). A possible circuit schematic for the computation module is discussed later in relation to FIG. 8D.

In this specification, the subject is a person or other living animal making use of respiratory analyzers according to the present invention. A health professional is a fitness consultant, dietician, doctor, coach, trainer, or other person who may provide feedback, encouragement, or advice to the subject.

FIGS. 2A–D illustrate further designs for a respiratory analyzer. FIG. 2A shows flow module 100 comprising respiratory connector 102, in this case including a mouthpiece 104. Cable 106 connects the flow module to a remote computation module (not shown). The support harness 109 has two holes 106 and 108, through which the ends of the flow module protrude, allowing support of the flow module by the support harness. In other embodiments there may only be one hole, through which one end of the flow module protrudes.

FIG. 2B shows a flow module 110 seated in the support harness 112. The support harness comprises a flexible material, such as an open mesh stretchy fabric. Cable 114, connecting the flow module and computation module (not shown), passes through flexible (e.g. fabric) cable guide 116 supported on the support harness. A window to the oxygen sensor is provided at 118. The atmospheric port is partially shielded by a wind guard 120. A logo 119 may be embroidered or otherwise disposed on the harness.

In other embodiments, the support harness can comprises a rigid part, having one or two holes by which the flow module can be supported, and a flexible part adapted to be connected around the head, or connected to straps which can placed around the subject's head.

FIG. 2C shows a flow module 122 held in place by support harness 110, comprising one or more straps with adjustable closures 112, for example a hook and loop closure such as Velcro®. A separate nose clip 116 is also provided. A filter module, holding a filter, is provided at 100.

FIG. 2D shows a top view of part of a respiratory analyzer, showing a flow module 132 held by support harness 134, with mouthpiece 136 visible. The mouthpiece is on the subject side of the support harness.

FIG. 3A–C show a further embodiment of an improved respiratory analyzer. FIG. 3A shows flow module 140 having a flow connector 144 and mouthpiece 142.

Straps 150 and 152 (which may be two ends of the same strap encircling the head) connect to flow module 140 using clips 154 and 156. The clips slot into clip receivers in the housing of flow module 140.

The flow module may have a separable mouthpiece for improved hygiene, be a unitary structure, and/or may further comprise a filter.

FIG. 3B shows straps 150 and 158 supporting the flow module 140, through connections using for example support clip 156. The closure 160 may be hook and loop, a buckle, or some other adjustable closure.

FIG. 3C shows a top view of the flow module 140, showing oxygen sensor 160, mouthpiece 142, and flow connector 144.

The clip forming the support mechanism for the flow module also serves as a grille for the atmospheric port. The flow pathway of the flow module is in fluid communication with the atmosphere through holes such as hole 146 in support clip 156.

FIG. 4A shows flow module 180 supported by support harness 182, cable 184 electrically connecting the flow module to a remote computation module (not shown), the cable being guided by cable clips 186 and cable guide 188. The support harness has holes such as hole 196, for ventilation and cooling of the subject's head, subject comfort, and reduced weight. The support harness connects via a D-ring 190 to head strap assembly 194, which has tab 192 pushing through the D-ring and closing on itself, e.g. through a hook and loop closure.

FIG. 4B shows holes 198 and 200 in the support harness 182 which support the ends of the flow module 180. Material for at least part of the support harness, such as regions 182*a* and 182*b* shown in FIG. 4B, comprises a sandwich material having a multi-layer structure comprising a flexible metal film sandwiched between two nonmetallic materials, such as fabrics.

FIG. 4C shows a section of the sandwich material 202 comprising a backing material such as a fabric 208, a flexible metal film 206, and neoprene layer 204. The materials of the sandwich materials are connected by snap together two-part connectors 210 and 212, in which component 210 pushes into component 212. The sandwich material components can be inter-connected by any convenient method, such as glue, heat-bonding, stitching, staples, ultrasonic welding, laminating, or other attachment method.

FIGS. 5A–C show another embodiment of a respiratory analyzer. FIG. 5A shows a flow module 220 supported by support harness 232 through gasket 224. The support harness functions in part as a mask. The support harness 232 comprises a mask portion 228, having an internal metal part within a stitch and turn seam pocket, defined by seams such as seam 230, so as to maintain a mask shape. The flow module has an oxygen sensor window 226, and atmospheric port 222. The support harness further comprises elastic webbing 236 functioning as a cable guide, strap 240, and outer sealing and comfort material 234.

FIG. 5B shows the flow module 220 having a connector port 242 that protrudes through gasket 224 and mask 244, through which respired gases pass, and providing a fluid communication between the flow pathway and the mask. A disposable filter or mask liner 246 is provided.

FIG. 5C further shows flow module 220 supported by gasket 224 and support harness 232. Elastic webbing 236 on the support harness, functioning as a cable guide, supports cable 248 which electrically connects the flow module 220 and a computation module (not shown). Strap 240 connects to additional strap harness 252. The fitting around the head is adjustable using adjustable closures 250 and 254, which may, for example, comprise hook-and-loop or adjustable strap closures. For illustrative purposes, cable 248 was not shown in FIG. 5A.

FIGS. 6A–C show another embodiment of an improved respiratory analyzer. FIG. 6A shows flow module 280, having atmospheric port 282, supported by support clamp 284. Straps such as strap 288 clip onto the support clamp 284 to hold the support clamp in position, the support clamp supporting the flow module 280 and mask 308. Strap 288 has a mushroom clip 290 which is adapted to pass through a keyhole clip receiver 286 of the support clamp. A cable 306 electrically connects the flow module to a computation module (not shown). The flow module 280 has a flow pathway in fluid communication with the mask 308, which is supported by the support clamp, so that as the subject respires, respiratory gases pass through the mask and through the flow module.

FIG. 6B shows flow module 280 having a housing having a generally cylindrical shape, so as to be supported by the support clamp 284. The housing of flow module 280 has a section of reduced external cross-sectional area, as shown at 292, which passes through and is held by the support clamp.

FIG. 6C shows flow module 280 supported by support clamp 284, strap 296 having support pad 298, and strap 300. The straps are connected to holes, such as keyhole clip receiver 286, in the support clamp by connection adapters 292 and 304. Alternatively, straps with mushroom clips, such as shown at 290 in FIG. 6A, can be used. Cable 306 connects the flow module to a remote computation module not shown in FIG. 6C.

FIGS. 7A–B show another embodiment of a flow module shown generally at 300. FIG. 7A shows a flow module having housing 302, atmospheric port 304, and cable dock 306 which forms an electrical interface with cable 310 through cable plug 308. Respiratory connector 318, having mouthpiece 316, has a connector tab 314 which slots into slot 312 of the flow module, and also forms a spit reservoir. This forms a rigid mechanical connection between the flow module and the respiratory connector. When the flow module and respiratory connector are connected, the filter 320 is held in place between them. The cable may be a serial connector providing an electrical connection and data communications between the flow module and a remote computation module.

FIG. 7B shows respiratory connector 318 pushed into flow module 302, so as to form a rigid mechanical connection. Strap 324 is provided with clip 326 which clips into the housing 302 of the flow module. Respired air passing through atmospheric port 304 then passes through holes such as hole 328 in clip 326. An oxygen sensor window 322 is also shown.

Figure 8A:
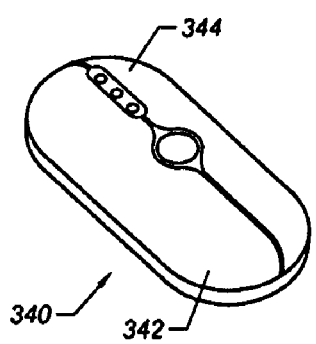
FIGS. 8A and 8B show a computation module.
Figure 8B:
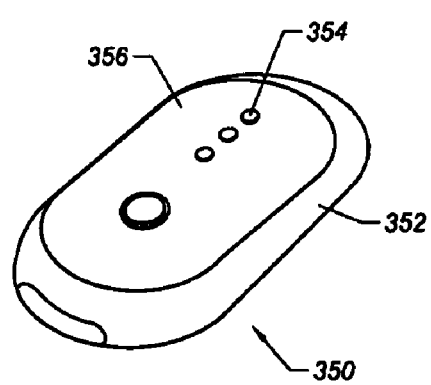
Figure 8C:
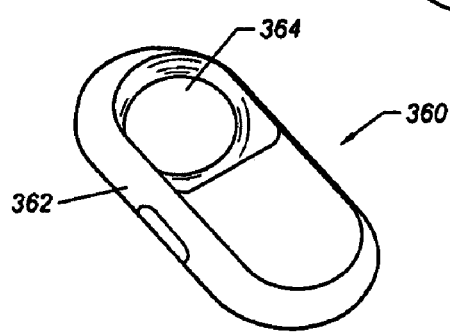
FIG. 8C shows a computation module.

FIGS. 8A–C illustrate computation module embodiments, which may also be referred to as pods. FIG. 8A shows a computation module 340 having housing 342, and a plurality of indicator lamps 344, and a central switch (such as an illuminated power switch) 346. The indicator lamps may be light emitting diodes (LEDs). The housing can be provided with reveal lines to tie into other indirect calorimeter products.

FIG. 8B shows computation module 350 having housing 352, and indicator lamps 354 (such as light emitting diodes) mounted under a high gloss back painted lens 356.

FIG. 8C shows computation module 360 having housing 362, further comprising a liquid crystal display under lens 364.

Figure 8D:
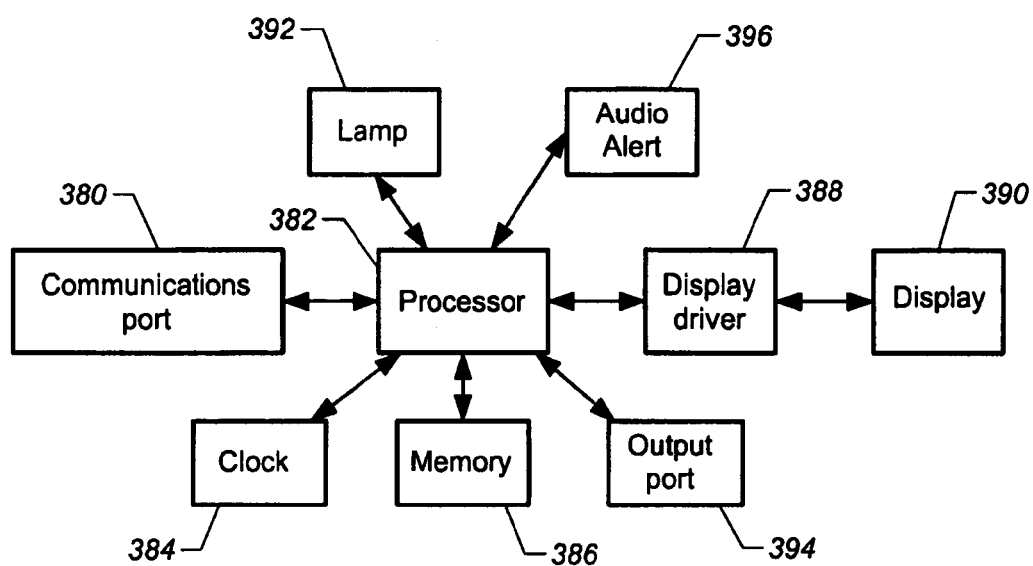
FIG. 8D shows a schematic of a computation module.

FIG. 8D shows a schematic of a possible computation circuit for use in a computation module. Communication port 380 can allow signals from the flow module to be directed to the processor 382. The communication port can also receive signals from sensors and transducers in the flow module, and control commands for sensors and transducers can also be communicated to the flow module if necessary. Processor 382 is in communication with clock 384, memory 386, output communication port 394, display driver 388 which drives display 390, audio alert 396, and indicator lamp 392.

A software program may be executable on the processor of the computation circuit, operable to determine a respiratory parameter (such as oxygen consumption) or metabolic rate. This is discussed in more detail in a following section.

Figures 9A, 9B, 9C, 9D:
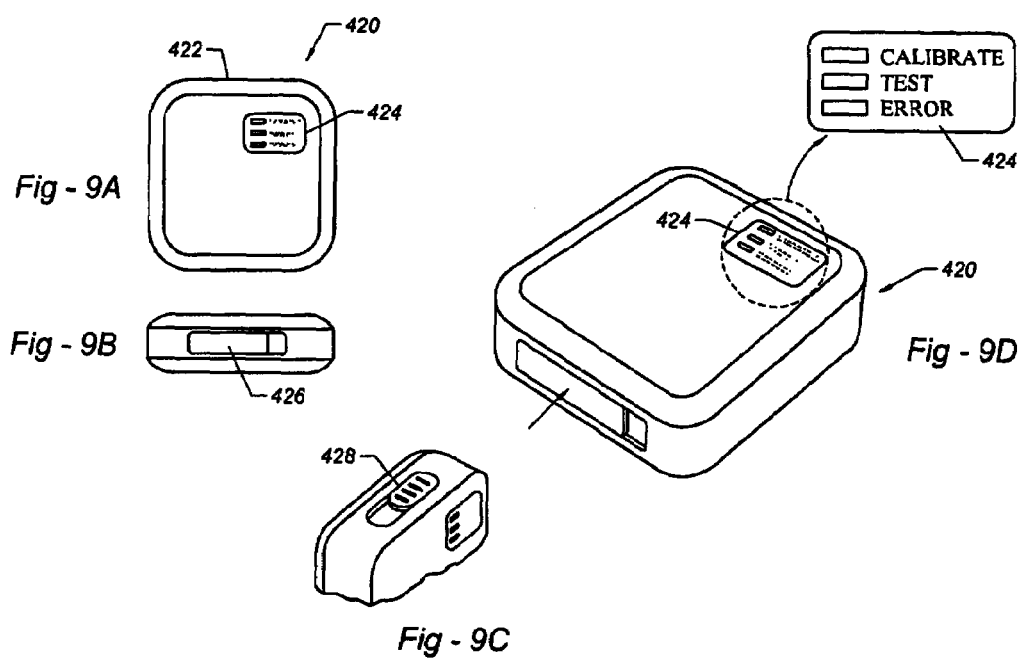
FIGS. 9A–9D show another configuration of a flow module.

FIGS. 9A–C show further embodiments of a computation module. FIG. 9A shows computation module 420, having housing 422, and LED feedback area 424. The LED feedback area comprises a plurality of indicator lamps providing an indication to the subject of operating status, for example calibration, test, exercise status, goal achievement, proximity to goal achievement, or error indications.

The computation module can have a sandwich construction, having a stamped aluminum top and bottom and an injected molded central region. A recessed LED feedback area can be provided, along with an elastomer covered serial socket cover.

FIG. 9B shows a side or end view of the computation module, showing the location of electrical connector, in this example covered by connector protector 426, which may be a serial cable socket. A cable from the flow module can be inserted into this socket.

FIG. 9C shows a top view of the computation module, showing position of the power (on/off) switch 428. The on/off switch may be omitted, and the device provided with an auto turn off feature. The location of the features on the housing can be changed as desired.

FIG. 9D shows an oblique view of the computation module, and more detail of the LED feedback area 424.

Figure 10A:
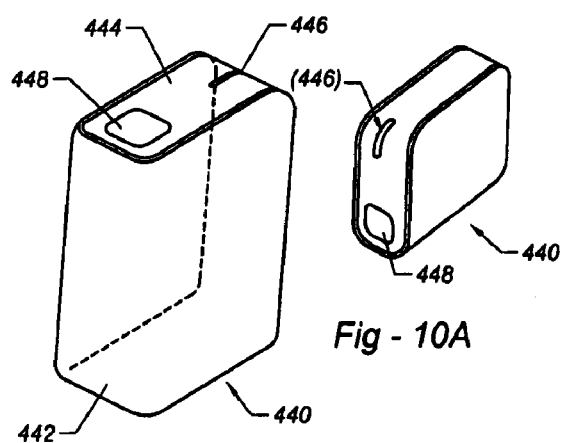
FIGS. 10A–10C illustrate another design of a flow module.
Figure 10B:
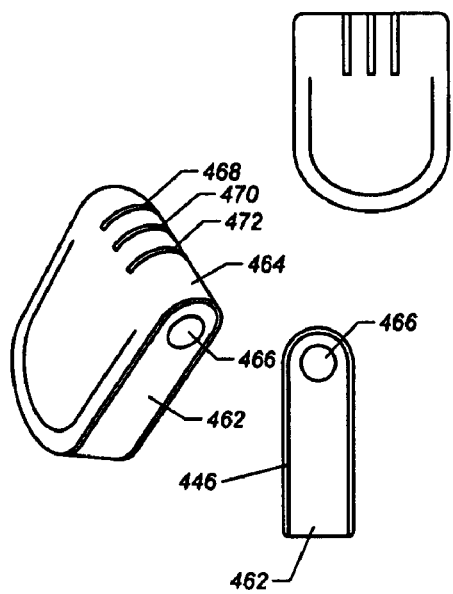
Figure 10C:
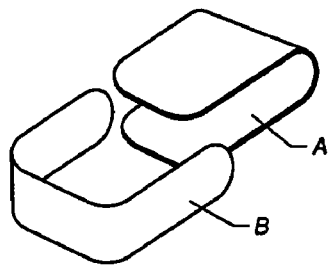

FIGS. 10A–C show further designs of a computation module. FIG. 10A shows a computation module having a two-part housing comprising interlocking pieces 442 and 444. Housing piece 444 supports indicator lamp 446 (a wrap-around light pipe) and on/off switch 448.

FIG. 10B shows a design of computation module 460, again having a two-part housing comprising interlocking housing parts 462 and 464. Housing part 464 supports three indicator lamps 468, 470 and 472, and switch 466.

FIG. 10C illustrates the two-part housing concept in an outline fashion, using two parts A and B.

Figures 11A, 11B:
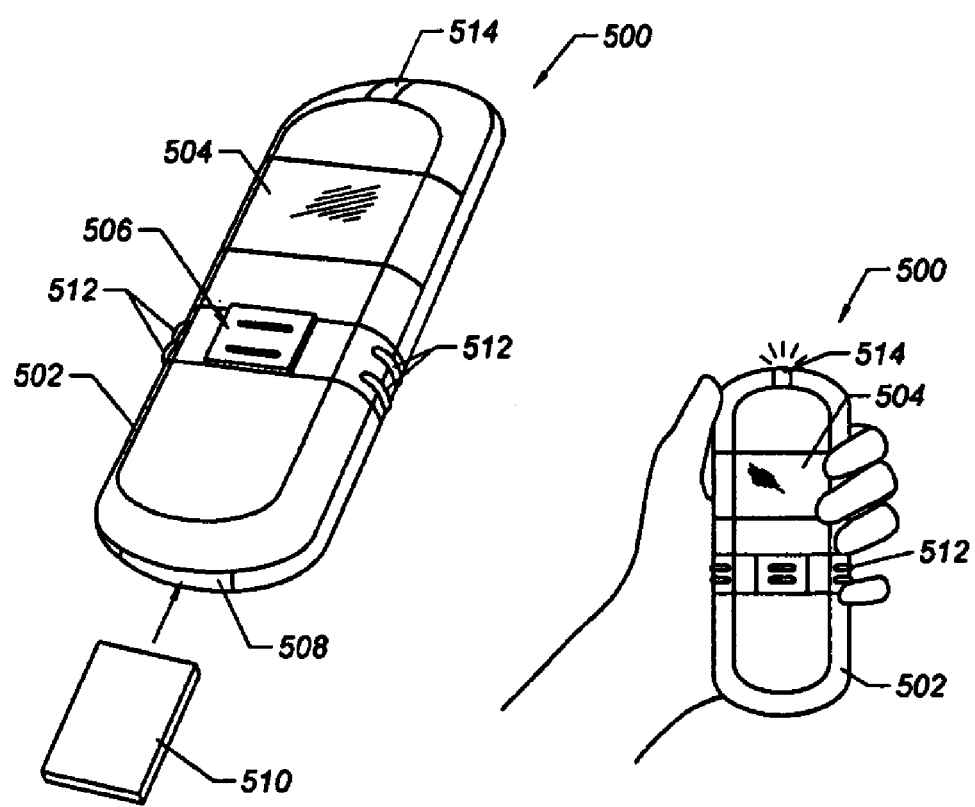
FIGS. 11A and 11B show a flow module having a memory card reader.

FIG. 11A illustrates a further embodiment of a computation module 500, having housing 502, liquid crystal display behind lens 504, on/off switch 506, and memory card slot 508 adapted to receive memory card 510. Housing 502 has grips 512 (which may be molded into the housing, comprise rubber inserts or similar), and lamp (light emitting diode) 514.

FIG. 11B is a further illustration of the computational unit 500.

Figure 12:
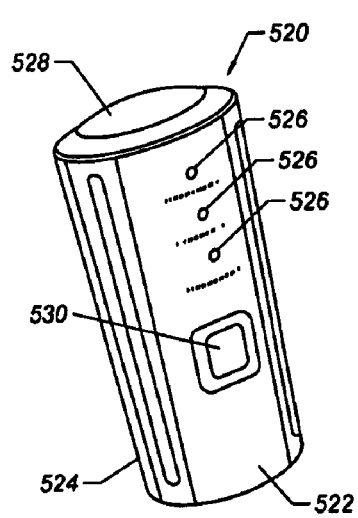
FIG. 12 shows a memory module having rubber sides.

FIG. 12 shows a computation module 520 having housing 522 with molded rubber sides 524 and a metal faceplate, indicator lamps 526, main lamp 528, and main button (power switch) 530.

Figure 13:
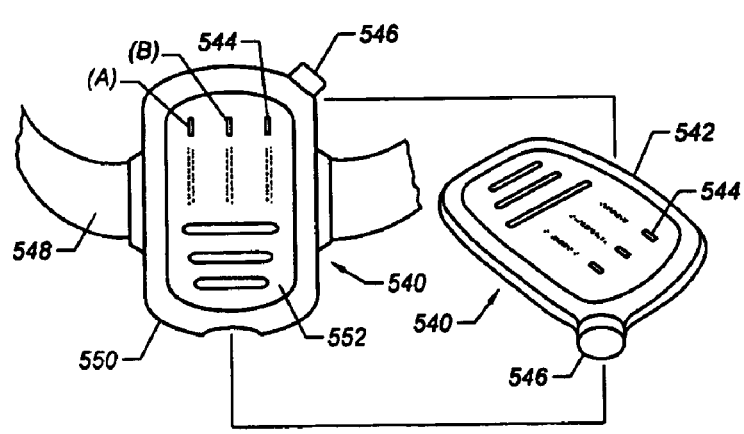
FIG. 13 shows a memory module having a strap mounted design.

FIG. 13 shows a computation module 540 in two views A and B, having housing 542, indicator lamps 544, and main button 546. In this example, the computation module is mounted on strap 548 which can encircle the wrist, the torso or other body part of the subject. The computation module may also comprise an accelerometer and/or a pulse rate sensor. The housing 542 comprises a rubber case 550 with metal faceplate 552.

Figure 14:
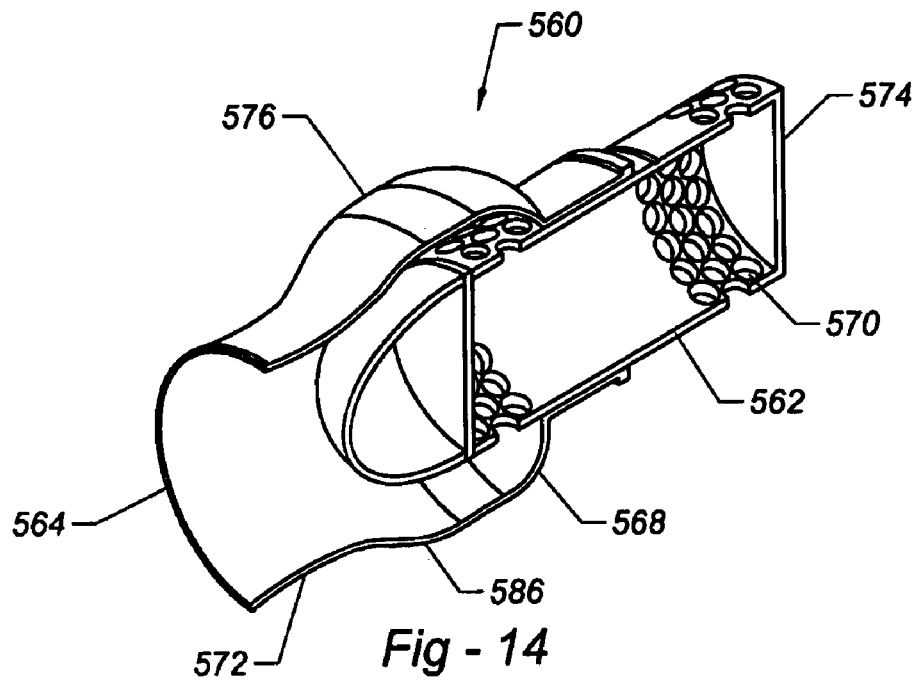
FIG. 14 shows a flow pathway configuration.

FIG. 14 illustrates a flow pathway configuration, shown generally at 560, which can be used within flow module embodiments. Exhaled breath passes through respiratory connector flow pathway 564 into first chamber 586, then passes through first plurality of apertures (or array of openings) 568 into flow tube 562. The exhaled gas then passes through second plurality of apertures 570. The second plurality of apertures is in fluid communication with an atmospheric port of the flow module. One plurality of apertures has 60×3 mm diameter holes in three rings around the flow tube Nose cone 572 conditions the flow of gas, for example by reducing turbulence and eddies. The flow tube 562 has end pieces 574 and 576. In other embodiments, the end pieces and nose cone can be omitted or otherwise modified, for example so as to allow respired gases to enter and exit a flow tube through a substantially axial path (for example, through an open end of a tube), or a combination of radial and axial paths. Inhaled gases pass in substantially the reverse direction to exhaled gases. Ultrasonic transducers may be supported by end pieces, or otherwise supported, so as to exchange ultrasonic pulses through at least part of the gas within the flow pathway.

Figure 15:
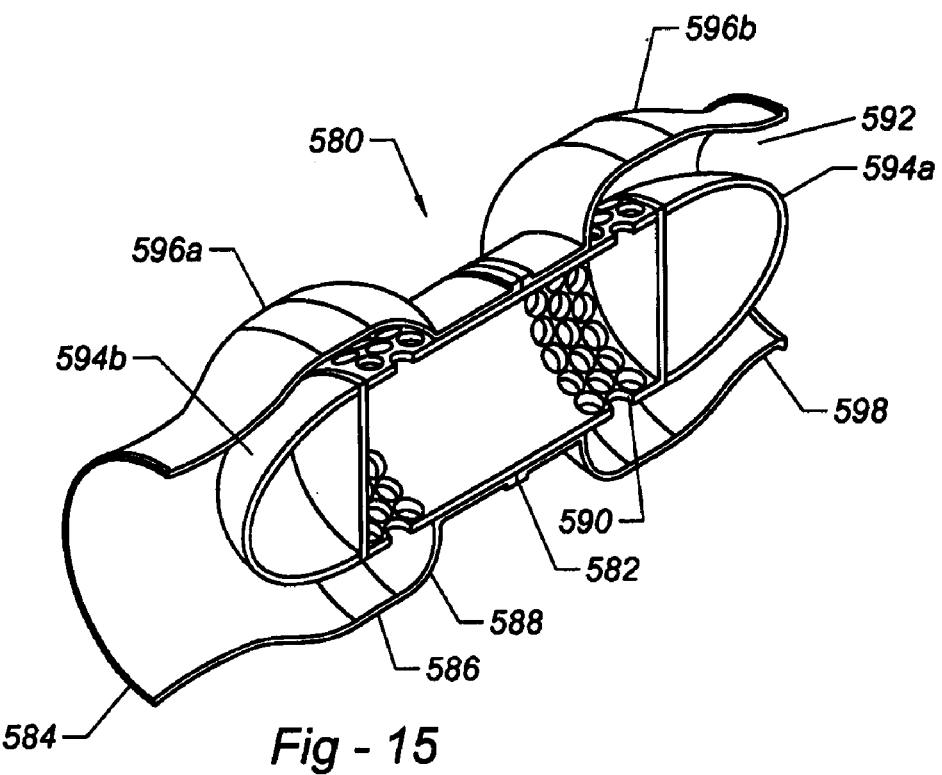
FIG. 15 shows a further flow pathway configuration.

FIG. 15 illustrates another flow tube configuration, shown generally at 580, which may be used within the flow module. As in FIG. 14, exhaled air enters first chamber 586 through respiratory connector flow pathway 584, for example from a mask or mouthpiece. The exhaled gas then enters flow tube 582 through the first plurality of apertures 588. Exhaled gas then passes along flow tube 582, exiting the flow tube through second plurality of apertures 590 into second chamber 592, which may be open to the atmosphere, shielded using wind guard 598.

The exhaled gas then exits through an atmospheric port within the housing of the flow module. Nose cones 594a and 594b are present to condition the flow of gases, and can be omitted. In other embodiments, flow tube end pieces 596a and 596b, and the nose cones, can be omitted or otherwise modified, for example so as to allow respired gases to pass through open ends of a flow tube.

Ultrasonic transducers can be located on the end pieces of the flow tube, so as to provide an ultrasonic flow meter, and a gas component sensor such as an oxygen sensor can be located within the flow pathway so as to provide a signal correlated with the partial pressure of a component of respired gases.

FIG. 16 shows a schematic of a flow configuration within a flow module, in essentially cross-sectional form but showing a surface of the flow tube so as to illustrate holes in the flow tube. The flow module shown generally at 600 has housing 616 and a respiratory port 604, which may be in fluid connection with a respiratory connector such as a mask or mouthpiece. Exhaled gases enter first chamber 606 (arrow A), passing through the first plurality of apertures 608 (arrows B and C) into the flow tube 602, then exiting through second plurality of apertures 610 into second chamber 612 (arrows D and E), then exiting through atmospheric port 614 (arrow F). Partition 618 divides the first and second chambers. Flow tube 602 has a substantially circular cross-section, and encloses a central flow pathway. The first and second chambers have regions concentric with the flow tube.

FIG. 17 shows another embodiment of the flow pathway through a flow module, in essentially cross-sectional form but showing a surface of the flow tube. Flow module 620 has housing 622, and respiratory port 624. Exhaled gases from a subject enter through a respiratory connector, such as a mouthpiece, pass through respiratory port 624, passes fluid path 625 into first chamber 626. Exhaled gas then flows into the flow tube 628 (arrows A and B), exiting through plurality of apertures 630 into second chamber 632 (arrows B and C). Exhaled gas then leaves through atmospheric port 636. The first and second chambers have regions concentric with the flow tube 628, and are separated by partition 623. The flow tube 628 encloses a central flow pathway for respired gases.

The nose cone 634 is present to condition the flow of gas, in particular inhaled gas. The schematic also shows the location of a pair of ultrasonic transducers, the first transducer 638 being supported at the end of the flow tube 628, and the second transducer 639 being supported within a protruding region of the housing.

Apertures in the flow tube are used to improve flow through the flow tube, reducing turbulence and eddies.

Figure 18:
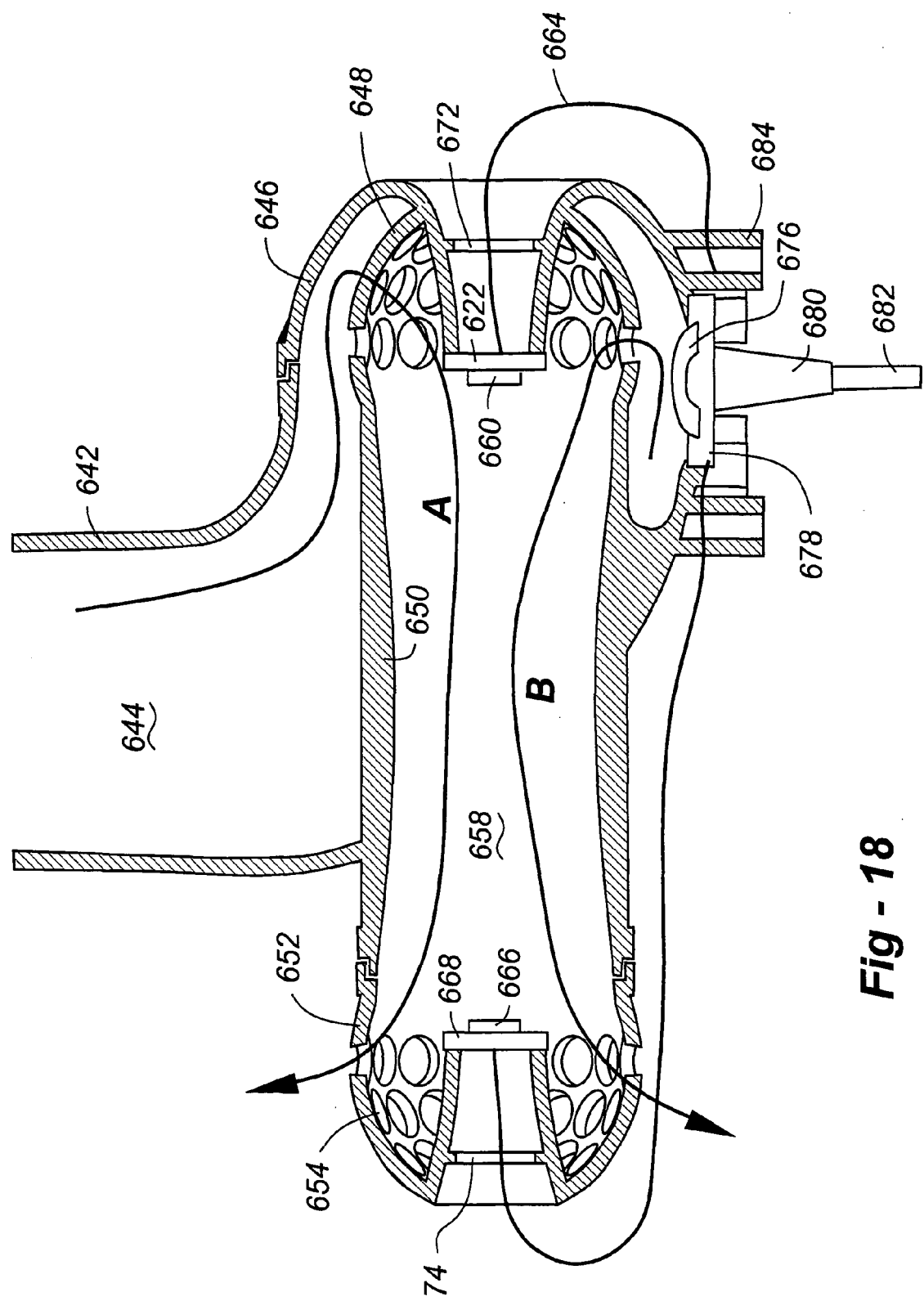
FIG. 18 shows a cross-section of a flow pathway, and associated components.

FIG. 18 shows a further embodiment of a respiratory analyzer in cross-section. Respiratory analyzer 640 comprises flow module housing 642, respiratory port 644, chamber 644a, first end assembly 646, first plurality of apertures 648, flow tube 650, second end assembly 652, second plurality of apertures 654, central flow pathway 658, first ultrasonic transducer 660, first transducer support 662, first transducer lead 664, second ultrasonic transducer 666, second transducer support 668, second transducer lead 670, first end piece 672, second end piece 674, oxygen sensor 676, flow module printed circuit board 678, cable connector 680, cable 682, and connector shield 684, which encircles the cable.

FIG. 8C shows a computation module.

Inhaled gases enter the central flow pathway 658 through second plurality of apertures 654, pass along the central flow pathway, pass through the first plurality of apertures 648, enter chamber 644a, then pass through respiratory chamber 644b and respiratory port 644, and enter the mouth and respiratory tract of the subject. The subject's mouth may contact the respiratory port, or a separate respiratory connector and/or filter module may be provided. Exhaled gases follow a reverse path shown by arrows A and B.

The respiratory port is approximately balanced with respect to the central flow pathway. An imaginary axis drawn through the center of the respiratory port intersects the long axis of the central flow pathway near the middle of the central flow pathway, allowing the weight of the respiratory analyzer to balanced around the center of the respiratory port for subject comfort.

The flow module housing 642 surrounds the respiratory port 644. The central flow pathway 658 is surrounded by a flow tube 650, formed within the housing. The housing also comprises first and second end piece assemblies 646 and 652, which may be removable to assist assembly, sterilization, maintenance, or component replacement.

The central flow pathway has a cross-sectional area which tapers from both ends towards a minimum at the mid-point of the flow tube, equidistant from the two ultrasonic transducers. The cross-section tapers from the ends to the mid-point, which helps condition flow through the flow pathway and increase the accuracy of ultrasonic flow rate measurements.

The ends of the central flow pathway are defined by the ball ends provided by end piece assemblies 646 and 652, the ball ends having the first and second plurality of apertures 648 and 654 respectively.

The opposed ultrasonic transducers 666 and 660 exchange ultrasonic pulses through respired gases within the central flow pathway. The ultrasonic transducers are supported so as to be within the laminar flow region of the flow tube. The housing end pieces are shaped so as to support the ultrasonic transducers away from turbulence generated by gases entering or leaving the central flow pathway. The transducers are advantageously supported within regions where axial flow (parallel to the long axis of the flow tube) predominates over radial flow. The transducers hence are supported within regions of substantially laminar flow, outside regions of turbulence associated with the tube ends.

The flow module printed circuit board supports the oxygen sensor in fluid communication with respired gases flowing through the flow module, and also provides electrical communication between the cable 682 and the ultrasonic transducers 660 and 666 through transducer leads 664 and 670. The flow module printed circuit board provides electrical communication between the oxygen sensor and the cable 682. The cable provides electrical communication between the flow module and a remote computation module (not shown). In one embodiment, the dead space of the respiratory analyzer is approximately 70 ml.

Figure 19:
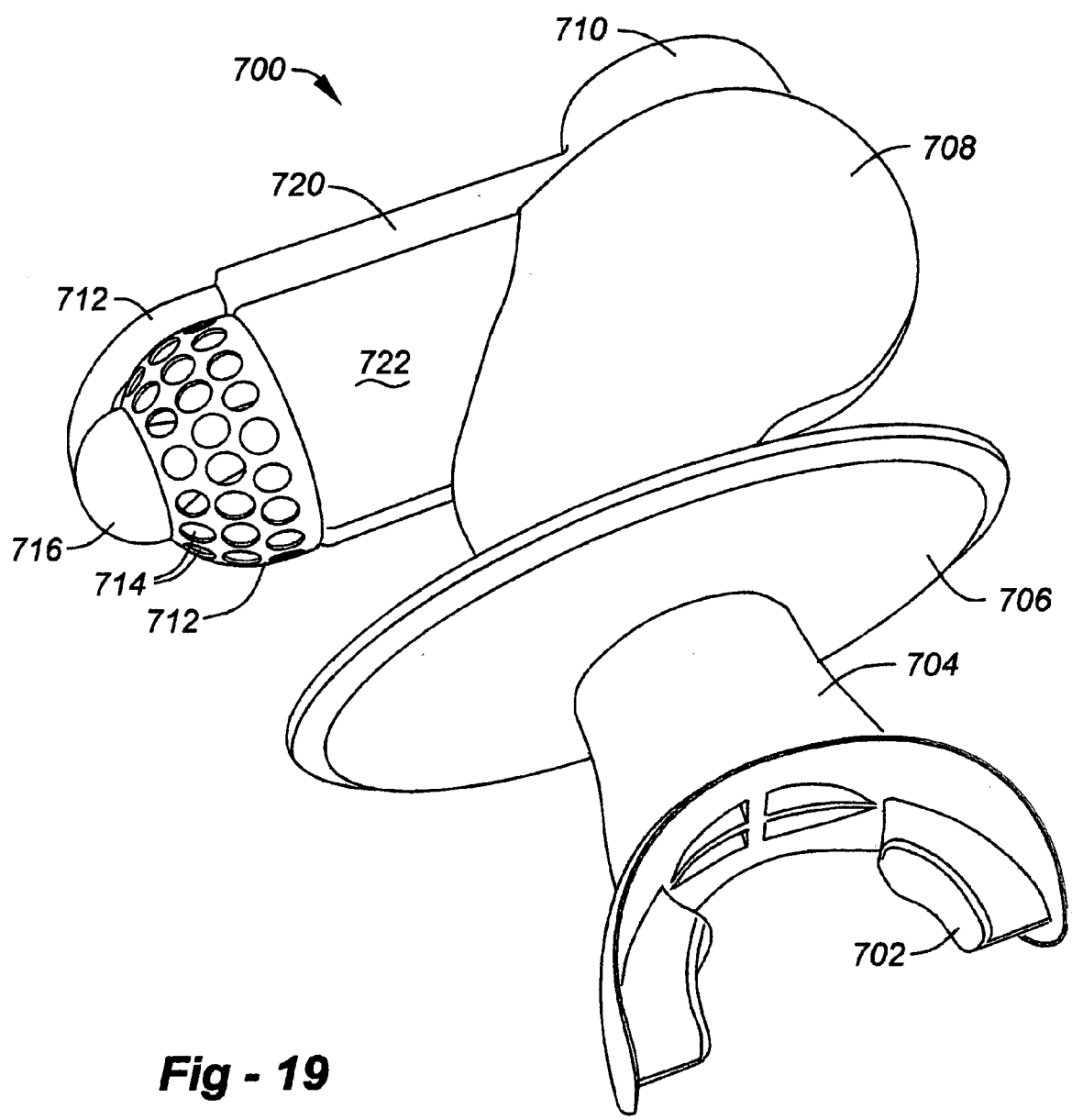
FIGS. 19 and 20 show flow pathway configurations.

FIG. 19 shows a view of a respiratory analyzer 700, which may have a cross-section similar to that shown in FIG. 18, comprising a respiratory connector 704 having a mouthpiece 702 and filter module 706, a flow module housing 708, connector shield 710, ball end 712, plurality of apertures 714, lead guide 718, lead channel 720, end cap 716, and flow tube 722. The lead guide and lead channel enclose a transducer cable.

Figure 20:
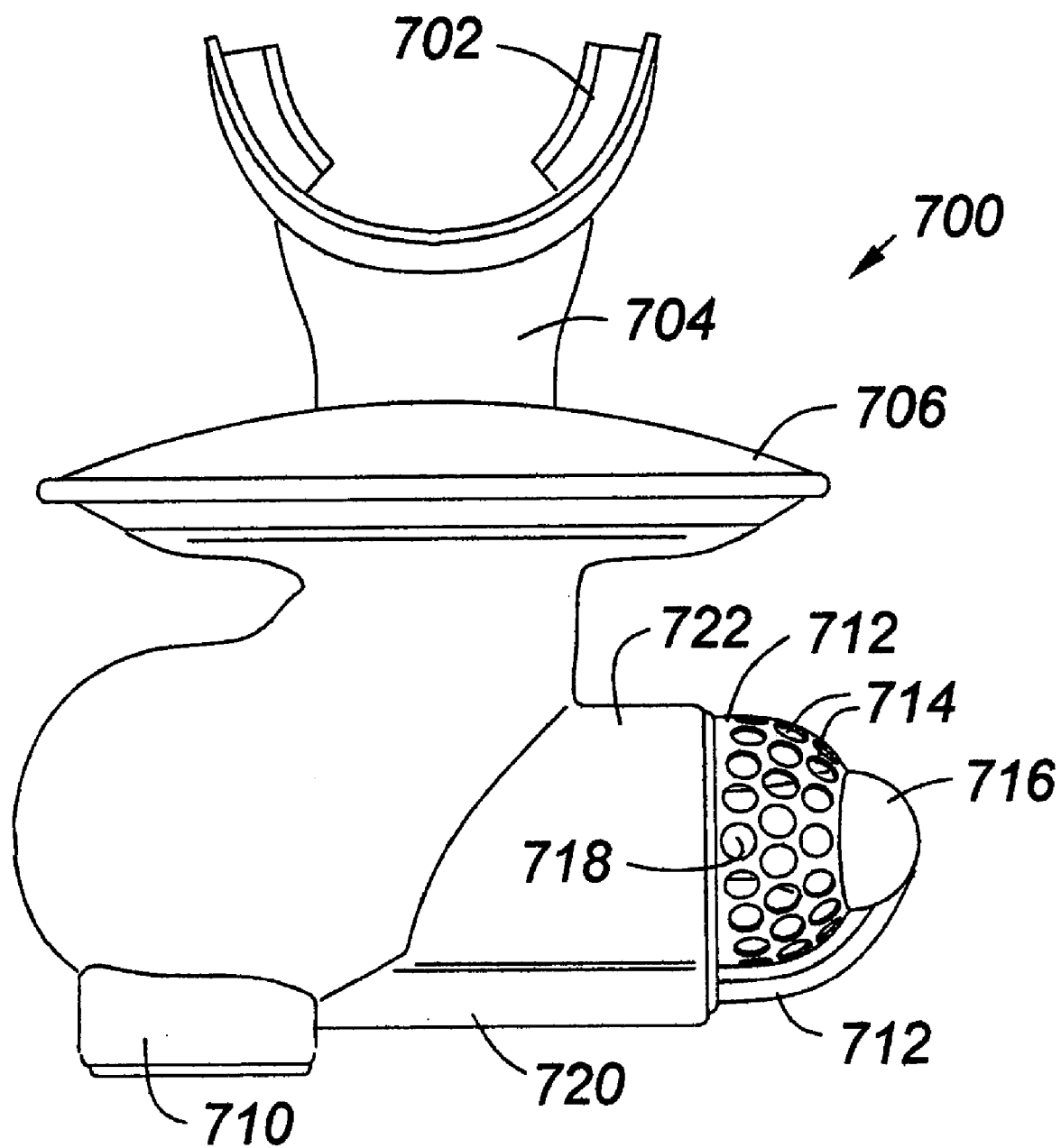

FIG. 20 shows another view of the respiratory analyzer 700, showing respiratory connector 704 comprising mouthpiece 702 and filter module 706, and flow module housing 708. Other elements are as described in relation to FIG. 19.

Figure 21:
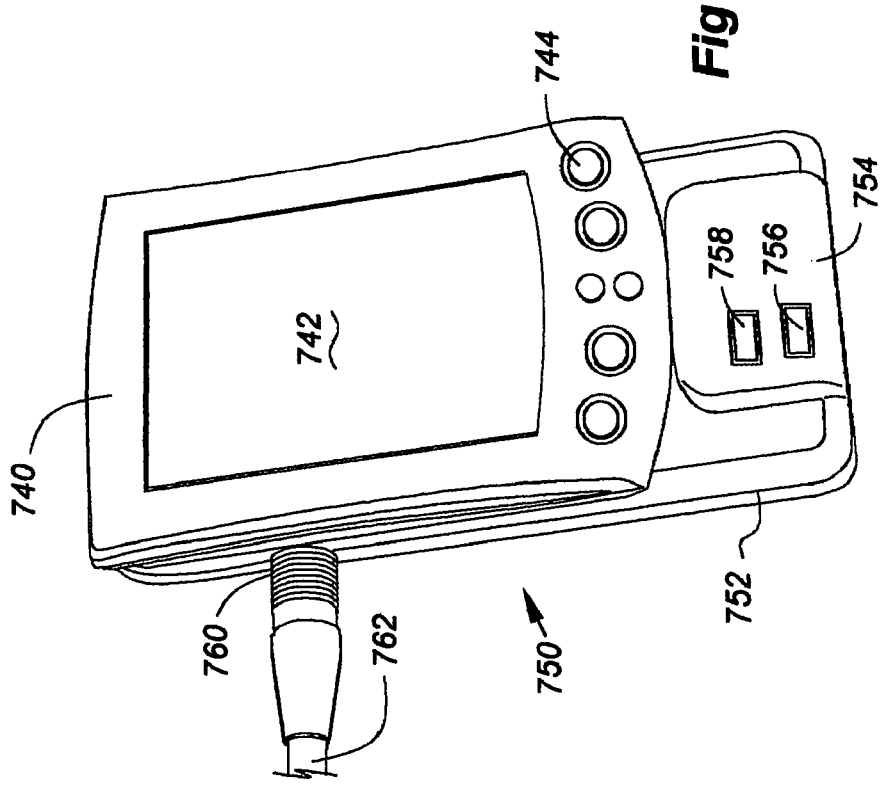
FIG. 21 shows a system including a personal digital assistant (PDA).

FIG. 21 shows a personal digital assistant 740, having display 742, and data entry mechanism 744, supported by a support module 750. The module 750 has a housing 752, power button 756, operational mode button 754, connector module 758, and cable connector 760, receiving cable 762 from a remote flow module (not shown).

Figure 22:
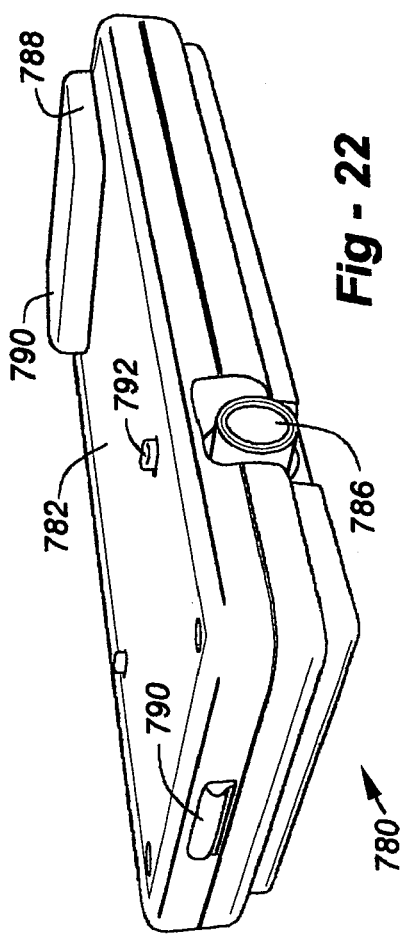
FIG. 22 shows a module for supporting a PDA.

FIG. 22 shows a support module 780, having a housing 782 having a support region 784 which can mechanically support a personal digital assistant, a cable connector 786, connector module 788, release button 790, and support protrusions 792. A PDA is placed on support region 784, and is in communication with the support module through an appropriately located electrical connector (for example, on the connector module) or through a wireless communication method. The PDA is held in place by support protrusions 792. Pressing release button 790 causes the PDA to be disengaged from the support protrusions. The support module may comprise an internal power supply, such as batteries.

A support module and a PDA cooperate to provide the functions of a computation module. The display of a PDA, for example display 742, can be used to show metabolic rate, VO2, or other parameters.

Figure 23:
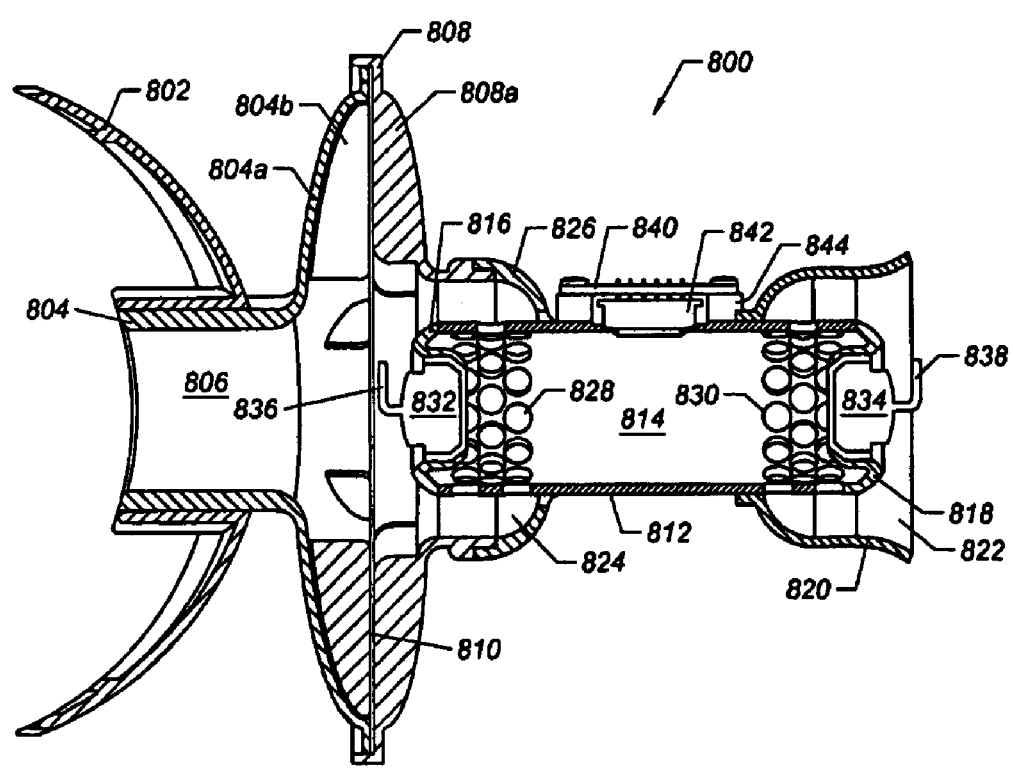
FIG. 23 shows a cross-sectional view of a flow module.

FIG. 23 illustrates a further embodiment of a respiratory analyzer according to the present invention. A flow module, shown generally at 800, comprises a mask 802, a mouthpiece member 804 enclosing a respiratory port 806, a filter 810 supported between the mouthpiece member 804 and a filter module member 808, a flow tube assembly 812 enclosing a central flow pathway 814, a first flow tube end piece 816, a second flow tube endpiece 818, a wind guard 820 enclosing an atmospheric chamber 822, a concentric chamber 824 enclosed by flange 826 extending from the flow tube assembly 812 and the filter module member 808, a first plurality of apertures 828, a second plurality of apertures 830, first ultrasonic transducer 832, second ultrasonic transducer 834, first ultrasonic transducer cable 836 and second ultrasonic transducer cable 838 (portions only shown), oxygen sensor printed circuit board 840, oxygen sensor 842, and PCB support 844.

The replaceable filter 810 is held in place between a flared part 804*a* of the mouthpiece member 804 and the filter member 808. Both the flared part of the respiration member 804*a* and the filter member 808 are provided with fin ribs (such as 804*b*, 808*a*) to prevent the filter from flapping. In other embodiments, the mouthpiece member may be essentially a tube, and a filter module provided to secure the filter in position.

The opposed ultrasonic transducers 832 and 834 are in ultrasonic communication so as to determine flow rates of gases passing through the central flow pathway. The oxygen sensor 842 has a sensing region providing a fluorescence signal correlated with a partial pressure of oxygen within the central flow pathway.

The central flow pathway is in fluid communication with the concentric chamber through the first plurality of apertures, and in fluid communication with the atmosphere through the second plurality of apertures 830.

As a person inhales, inhalation gases pass through the atmospheric chamber 822 and into the central flow pathway 814 through the second plurality of apertures. Inhalation gases then pass through the central flow pathway, through the first plurality of apertures into the concentric chamber, through the filter and the respiration port to the mouth of the person.

The wiring configuration is not shown in detail. FIG. 23 only shows part of the ultrasonic transducer cables, and does not show electrical connections to the oxygen sensor. In one embodiment, coaxial cables connect the ultrasonic transducers to electrical circuitry on the oxygen sensor printed circuit board (PCB), and a cable is then provided between the PCB and the computation module. In use, a cover member would be provided to cover the PCB, as discussed below.

In this configuration, the flow tube is oriented outwards from the mouth of a subject. This configuration was found to provide more accurate flow rate values.

Figure 24:
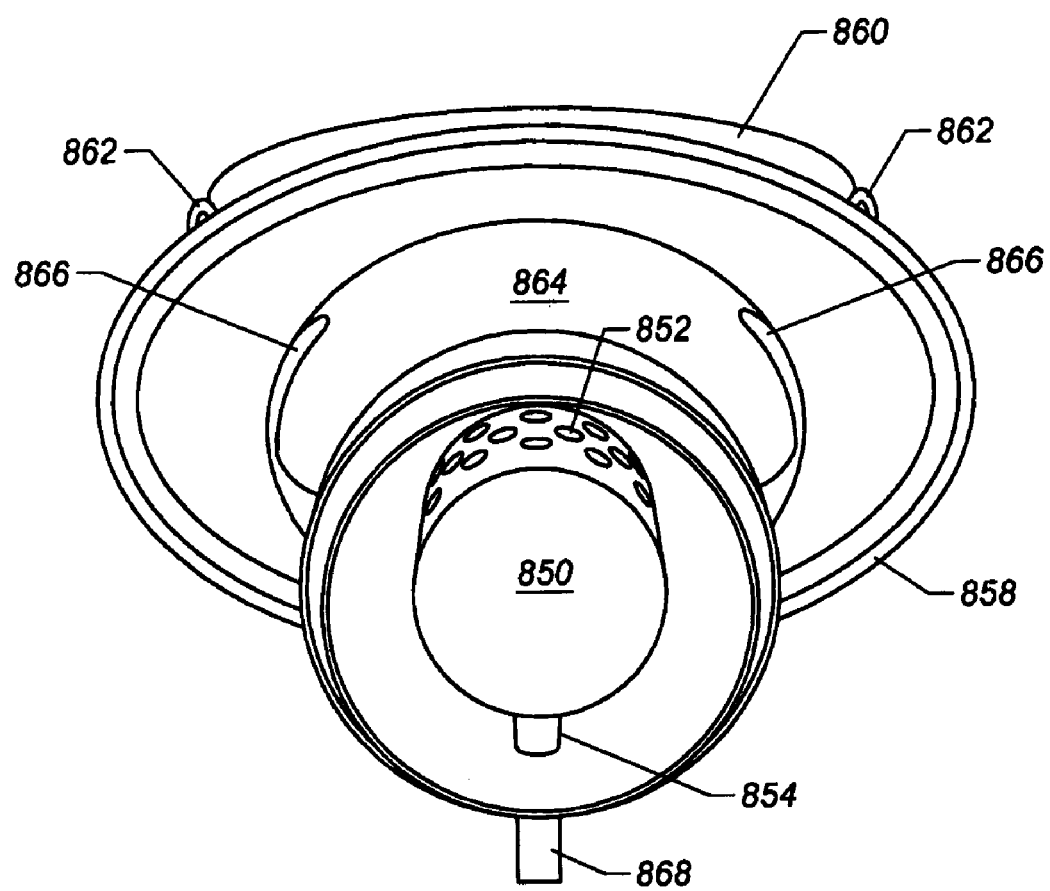
FIG. 24 shows an end view of a flow module.

FIG. 24 shows an end view of a respiratory analyzer according to the present invention, which may have a configuration similar to that of FIG. 23. The end view shows a flow tube end assembly 850 having a plurality of apertures 852, an ultrasonic transducer cable 856, a wind guard 854, a filter module member 858, tabs 862 for connecting a strap, part of a mask 860, and a cover member 864 (which if shown in FIG. 23 would provide a cover for the PCB) having quick release press buttons 866. Removal of the cover member facilitates access to the filter module. Cable 868 connects to the computation module.

B. Respiratory Analyzer Operation

A person can measure their metabolic rate during exercise, through determination of consumed oxygen volume, carbon dioxide production, or some other method. The determination of consumed oxygen volume is discussed at length in U.S. Pat. No. 6,468,222 to Mault et al. Operation of ultrasonic transducers and an oxygen sensor can be as described in U.S. Pat. No. 6,468,222. Flow modules can also include temperature, pressure, and humidity sensors.

Using respiratory analyzers according to the present invention, inhaled and exhaled oxygen volumes can be determined by integrating flow rates (as determined using a pair of ultrasonic transducers) with oxygen partial pressure (determined using a fluorescent oxygen sensor) in respired gases. Inhaled oxygen volumes can also be determined from inhaled volumes and a determined or assumed value of inhaled oxygen concentration. In other embodiments, metabolic rate can be determined by integrating exhalation flow rates with carbon dioxide partial pressures in exhalations so as to determine carbon dioxide production. In other embodiments, both oxygen consumption and carbon dioxide production can be determined. In this case, respiratory quotient can be determined, for example as a function of time during an exercise.

Respiratory analyzers according to the present invention can also be used to determine other respiratory parameters such as $VO_2$ max. Heart rate and $VO_2$ can be determined together as a function of exercise intensity, to obtain a correlation between them.

The flow module or computation module may also comprise data ports for receiving data from physiological sensors and activity monitors. A software application program can be executed by a processor within the computation module, as described in more detail below.

In other embodiments, some or all of the functions of the computation module may be included within the flow module, and the flow module and computation module may be combined into a unitary device. In other embodiments, certain components related to sensors and/or transducers may be located within the flow module, and other components located within the computation module.

C. Repiratory Analyzer Configurations

Respiratory analyzer configurations according embodiments of the present invention are discussed further below, including discussions of flow modules, computation modules, software, and feedback.

Flow Module

The gas component sensor may be an oxygen sensor, carbon dioxide sensor, or other respiratory component sensor. Respiratory components which may be detected and/or analyzed using embodiments according to the present invention include one or more of the following: oxygen, carbon dioxide, nitric oxide, organic compounds such as volatile organic compounds (including ketones (such as acetone), aldehydes (such as acetaldehyde), alkanes (such as ethane and pentane)), nitrogen containing compounds such as ammonia, sulfur containing compounds (such as hydrogen sulfide), and hydrogen. Reparatory analysis may also include detection of respiratory components diagnostic of health (such lung cancer, for example as disclosed by Phillips in U.S. Pat. No. 6,312,390, incorporated herein by reference), metabolism disorders, oral bacteria, stomach bacteria, other bacteria, asthma and other respiratory tract inflammations, and infections. Respiratory analysis can include detection of respiratory components administered to a subject, such as radio-labeled components, anesthetics, sedatives, drugs, and the like, or products of labeled compounds. Respiratory analysis can also include the analysis of inhaled gases, such as atmospheric components, pollutants, mists, aerosols, water vapor, other vapors, particulates, medically administered gases (such as nitric oxide, anesthetics), hazardous gases (such as carbon monoxide, volatile organic compounds), combustion products (such as smoke, particulates), other organic components (such as methane, other alkanes, petroleum products, and other volatile organic compounds), industrial chemicals, and any other inhaled species.

For example, embodiments of the present invention include a respiratory analyzer having both a carbon dioxide sensor and an oxygen sensor, along with circuitry operable to determine the respiratory quotient of the subject.

Flow meters which may be used in embodiments of the present invention include: ultrasonic sensors (e.g. using the transit times of ultrasonic pulses having a component of direction parallel to the flow pathway, sing-around sensor systems, and ultrasonic Doppler sensors detecting frequency changes in ultrasound as it propagates through a gas), differential pressure sensors (such as a pneumotach), turbines, pitot tubes, hot cable anemometers and other thermal methods, vortex shedding sensors (e.g. detecting vortices shed by an element in the flow path), and mass flow sensors.

In this specification, the term respiratory connector refers to a component of, or accessory to, the flow module, through which the subject breathes. The respiratory connector may comprise a mask, mouthpiece, face seal, nasal tubes, nares spreader, or some combination thereof, hygiene barriers such as pathogen filters, filter modules supporting a filter, reusable and disposable portions, indications of previous use, and the like. The respiratory connector may be separable from the flow module, for example for hygiene, replacement, sterilization, insertion of pathogen filters, or other purpose.

The respiratory connector may comprise two or more separate modules, for example a mouthpiece and filter module, or may be a unitary device, for example a disposable mask with a built in filter. The respiratory connector may also comprise indications of prior use as more fully described in co-pending applications to Mault et al. If a mouthpiece is used, a nose clip can be provided to help ensure all respired gases pass through the mouthpiece. The term respired gas refers to inhaled gas or exhaled gas.

In other embodiments, the flow through the nose can be neglected. For example, during intense exercise, it may be adequate only to analyze respiration through the mouth, neglecting flow through the subject's nose. A mask can also be adapted so as to allow respiratory analyzers according to the present invention to be used with other animals, such as horses, as discussed in more detail below.

In examples discussed above, respired gases enter a central flow path, bounded by a flow tube, through one or more arrays of apertures within the flow tube. In other embodiments, flow within the flow pathway can be conditioned by modifying the shape of one or both ends of a flow tube, for example by providing castellations or other modulations of the shape of the end of the flow tube, flaring the end of the flow tube so as to provide a bell-shaped opening, providing a plurality of structures around the end of the flow tube, such as radially aligned rods, axially aligned rods, or obliquely aligned rods, providing grooves or channels in the inner surface of the flow tube, providing axial rods along the length of the flow tube, adjusting the aspect ratio of an oval or elliptically cross-sectioned flow tube, providing microstructures or grooves on the inner surface of the flow tube, and the like.

The flow module may further comprise a processor adapted to interpret signals from sensors and transducers, circuitry to provide zeroing and calibration of the sensors and transducers, and circuitry to provide further processing of signals sent to the computation module (such as an analog to digital circuit, signal averaging, or noise reduction circuitry). In other embodiments, the flow module may comprise a flow meter, a gas sensor, and an electrical connector transmitting signals therefrom to a computation module.

In other embodiments, the composition of exhaled gas may be determined from density or mass flow measurements, which may be carried out using ultrasonic transducers or other methods known in the art. In other embodiments, inhalation gases may pass through a one-way valve into a respiratory connector through which the person breathes, and only exhaled gases pass through a central flow pathway for flow and/or composition determination.

The diameter of the central flow path is chosen to achieve a desired accuracy of flow rate measurement while not presenting appreciable resistance to respiration to the subject. Flow volumes are higher during exercise, and so the diameter of the central flow path can be increased so as to achieve similar flow rates as present in the indirect calorimeter described in U.S. Pat. No. 6,468,222.

Pluralities of apertures may be aperture arrays encircling one or both ends of the flow tube. For example, a plurality of apertures may include one, two, three or more rings of apertures encircling a flow tube, each ring of apertures including 5, 10, 12 or more apertures. The apertures may be circular apertures in the flow tube, or may be another shape such as square, hexagonal, oval, or other shape.

Computation Module

A computation module may include or be part of a computing device. A computing device may be a personal computer (such as a desktop computer, for example a computer at a fitness center or associated with an exercise machine), a portable computing device (such as a laptop computer, personal digital assistant (PDA), notebook computer, tablet computer, or game console), a portable electronic device incorporating the functionality of a computing device (such as a watch, other timepiece, telephone, other communications device, calculator, diet calculator, physiological sensor, activity monitor, or other electronic device), a suitably adapted device in the form of a body mounted accessory (such as clothing, shoe, visor, spectacles, earpiece, helmet, button, wristband, headband, jewelry, and the like), other adapted portable device (such as a writing instrument), an Internet appliance, a brain implant or other body implant (such as an implanted physiological sensor), a plug-in card or module adapted to be inserted or otherwise communicate with a personal digital assistant (PDA) or other computing device or cell phone, or other suitably adapted device.

A computation module (or support module, as discussed above) may be combined with a computing device (such as a PDA) so as to form a unitary device. For example, the computation module may comprise a plug-in card adapted to be inserted into or otherwise be mechanically associated with a personal digital assistant (PDA) or other portable computing device, or the computation module may transmit analyzed data to a computing device, or a computing device may comprise the functionality of the computation module.

The computation module may also be any portable electronic device, plug-in accessory for a portable computer or cell phone, comprise part of a helmet, be a wearable system. The computation module may be a modified device, such as a cell phone, physiological monitor, watch, heart rate sensor disposed on a strap, other accessory, activity monitor mounted on a belt or otherwise supported by the body of a subject, or some other device. The computation module may be handheld, or carried in a pocket, on a belt or strap, or be otherwise supported by the body of the subject. In other embodiments, the computation module may be carried by a fitness trainer, or be part of exercise equipment.

In other embodiments, the computation module may comprise an electronic device in wireless communication with a computing device. The computation module may be in wireless communication with the flow module.

The computation module may comprise a dedicated power supply, such as a battery, and can supply power to the flow module using, for example, a cable connection. Alternatively, the flow module may have its own dedicated power supply such as a battery. Power may be supplemented or provided by a solar cell in electrical communication with the flow module or computation module. A solar cell may be disposed either on the flow module, on the support harness or straps, or elsewhere on the subject, for example as part of a helmet, headband, or other headwear.

The computation module can be in communication with other devices through a communications network, such as a local area network or the Internet.

In other embodiments, the flow module and computation module can be combined in a unitary device. Communication between the flow module and the computation module can be wireless.

Software

A respiratory analyzer according to the present invention may be provided with a software application program, for example executable by a processor within the computation module, to calculate flow volumes, oxygen consumption, carbon dioxide production, metabolic rate, ventilatory equivalents, fat burning rate, fat burning total, carbohydrate burning rate, other metabolic parameters, respiratory frequency, airway inflammation evidence, peak flow, minute volume, respiratory quotient, or other respiratory parameters, or other physiological parameters such as cardiac output, for providing feedback to the subject (as discussed in more detail below). Other physiological parameters, such as heart rate, using data received from external sensors or other sensors within the analyzer, can also be displayed.

A software application program can be provided, executable by the processor, to calculate flow rates, flow volumes, oxygen consumption, carbon dioxide production, metabolic rate, ventilatory equivalents, fat burning rate, fat burning total, carbohydrate burning rate, other metabolic parameters, respiratory frequency, airway inflammation evidence, end tidal oxygen, end tidal carbon dioxide, end tidal nitric oxide, peak flow, minute volume, respiratory quotient (RQ), ventilatory equivalent (VEQ), or other respiratory parameters.

The software may also be operable to determine other physiological parameters such as heart rate and cardiac output (as described in more detail below), for viewing on a display. Physiological data can be received from external sensors, or sensors within the flow module or computation module.

A software program, executable by the processor of the computation module, may also be operable to determine exercise parameters such as exercise duration, calorie expenditure, maximum metabolic rate, average metabolic rate, activity energy expenditure, total oxygen consumption during exercise, maximum heart rate, fat burning, carbohydrate burning, and store parameters in a memory for future access. The software may also be operable to graph time dependent changes in exercise parameters, over the course of an exercise and over a time period including two or more exercises.

The software may also be operable to provide alerts and other feedback, as described below.

Feedback

The flow module and/or the computation module can include one or more alerts to provide feedback to the subject, for example feedback relating to the status of an exercise. An alert can be a lamp (such as colored light emitting diodes, or a bar-graph display), an audible alert (such a buzzer, chime, oscillator, and the like), a mechanical vibration actuator, odor generators, electrostimulators (such as electrodes disposed on the subject's body with circuitry adapted to apply an electrical signal to the subject's body), or other alerting mechanism.

Feedback provided to a subject during exercise, by computing device, exercise equipment, wrist-mounted monitor, or other electronic device, may comprise a colored light which may vary in emissive wavelength, number of illuminated elements such as a bar graph, brightness, flashing frequency, or some other parameter. Feedback may also comprise sound which may vary in frequency, tone, amplitude, modulation or some other acoustic parameter. Feedback may also be provided by an aroma generator, for example, which may provide a pleasant aroma if a certain exercise regime is achieved. Feedback can also be provided by mechanical vibration.

Feedback may be provided to the subject when the subject has achieved a certain exercise intensity level, has burned a certain number of calories, has burned a certain amount of fat, after a certain time, and the like. For example, a light, visual display, audible signal, vibration, aroma, or other alert may be provided to a subject if metabolic rate or other physiological parameter (such as heart rate) exceeds a predetermined threshold, falls below a predetermined threshold, comes within a predetermined range, or goes outside a predetermined range. Such feedback may assist a subject exercise within certain exercise regimes, such as cardiovascular exercise, aerobic exercise, or anaerobic exercise, as will be discussed further below. A radio, television, or other entertainment device, can be used to provide a subject with encouragement and feedback during an exercise. Feedback-producing devices can be in cable or wireless communication with the respiratory analyzer.

Metabolic rate, oxygen consumption, and other physiological parameters (such as heart rate and respiratory quotient) can be provided to the subject, for example on a display, during or after exercise, so as to allow the subject to control exercise intensity. Oxygen consumption can be displayed as a proportion of VO2(max), and heart rate can be displayed as a proportion of maximum heart rate (HR (max)). Metabolic rate and other physiological parameters may also be provided to a health professional, such as fitness advisor or coach. The health professional can provide feedback to the subject during exercise, for example by providing words of encouragement, instructions, feedback, and the like. Exercise data (physiological parameters, exercise parameters, or other data collected as the subject exercises) can be stored to a memory card within the fitness module, transmitted to a computation module, transmitted over a communications network to a remote device, or otherwise stored, displayed, or communicated to another device. A computer expert system can also be used to provide feedback.

A subject may use a data entry mechanism on the computation module to request an exercise program. For example, a subject may desire aerobic exercise. Feedback can then be provided to the person to allow the subject to maintain an exercise intensity in the upper level of the aerobic exercise intensity range.

A computation module can also communicate with the subject through an earpiece (or other audio generator), which may be part of the computation module or connected by a cable or wireless method to the computation module.

The subject may receive updates on metabolic rate and other parameters. Feedback to the subject can be provided by voice synthesis, for example audible expression of numerical data, audio modulation, selection and playing of appropriate music (such as fast tempo music if increased exercise intensity is required). The flow module may also be provided with a microphone, so as to allow the subject to communicate with a remote person, or the computation module using voice recognition techniques.

Exercise data can transmitted from a respiratory analyzer (or other device in communication with the respiratory analyzer) to a health professional. The method of transmission can be wireless (such as Bluetooth, IEEE 811, local wireless Ethernet, or infrared, acoustic, ultrasound, optical, or some other wireless method), or through a cable. The data can be visually displayed on a handheld computer in possession of the health professional, allowing the health professional to provide feedback to the exercising subject. This may be provided through spoken commands, which may be wirelessly transmitted to an earpiece or headset worn by the subject.

After completion of an exercise program, exercise data can be reviewed by the subject, reviewed by a health professional, transmitted to a personal computing device in possession of the subject, transmitted to a remote computer such as a server system, analyzed by software program executed by a computer (such an expert system), or otherwise displayed or analyzed. For example, the subject may consult with a health professional to discuss the data, determine future exercise regimes based on the data, and the like. Exercise data can include metabolic rate data, time, physiological parameters, activity monitor signals, ambient conditions, fat burning, exercise intensity, and the like.

Exercise data can be uploaded or otherwise transmitted to a personal computer for review by the subject or a health professional. A personalized exercise program may be generated based on the exercise data.

Exercise data, such as metabolic rate, maximum heart rate, or VO2(max), can be determined for a subject at intervals. Changes in exercise data can be presented graphically to the subject, to provide them with information on the progress of a health improvement program. An alert can be provided to the subject if heart rate is above a predetermined level, such as a certain fraction of the person's maximum heart rate.

Feedback can be provided to the subject based on their progress within a weight loss program. A subject can review exercise data on a personal computer. Exercise data, respiratory parameters, and other parameters can be communicated across a communications network, allowing feedback to be provided across the Internet or using an interactive television. A software application program on a personal computer in communication with the respiratory analyzer can also be used to provide feedback. Data can be used within an improved exercise program.

Exercise Machine System

Figure 25:
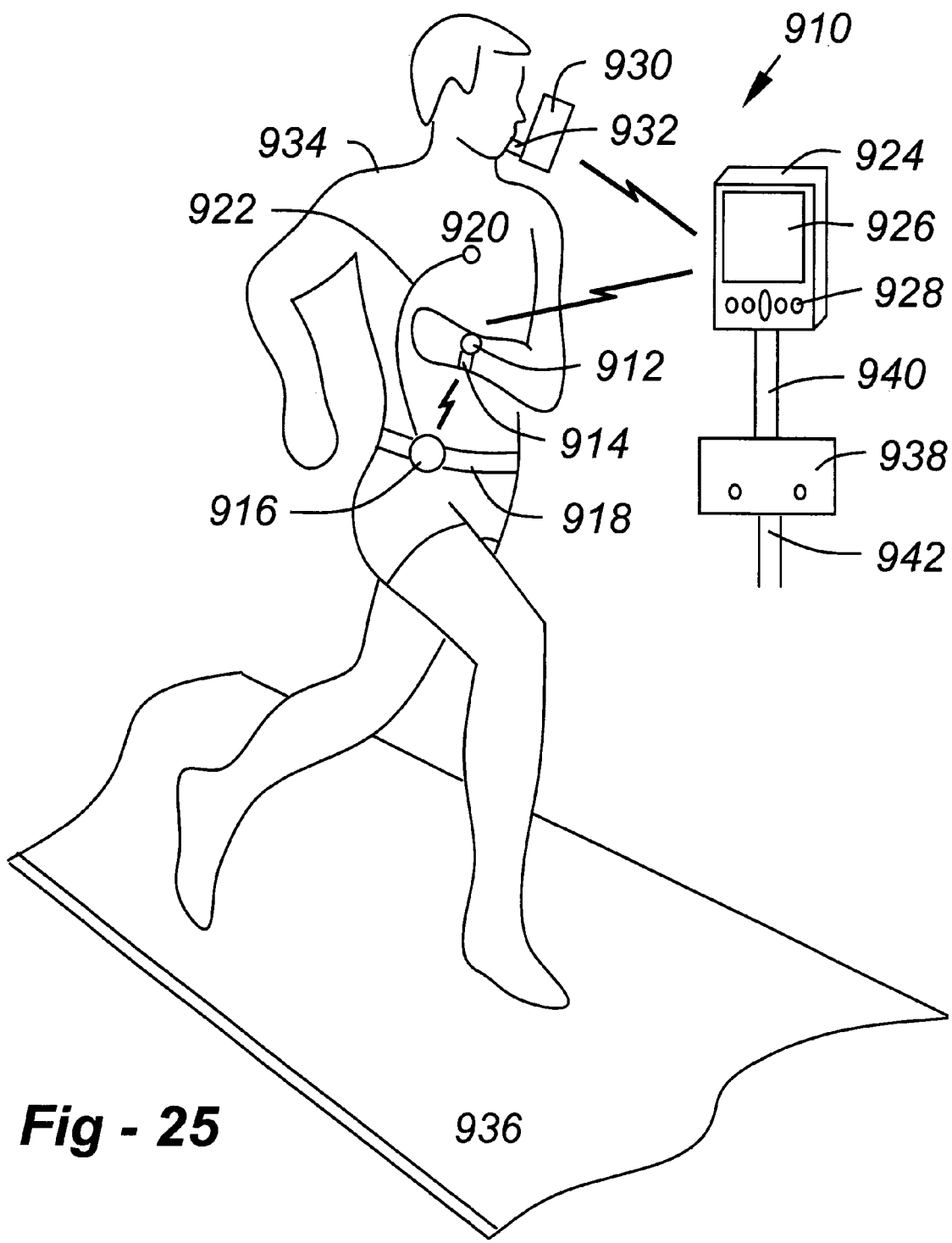
FIG. 25 shows an exercise system according to an embodiment of the present invention.

FIG. 25 shows an embodiment of a system according to the present invention. The system shown generally at 910 comprises a wrist-mounted monitor 912 supported by strap 14 around the wrist or arm of the subject, a torso-mounted activity monitor 916 supported by a belt 918, an electrode 920, a conductor 922, a computing device 924 having a display 926 and data entry mechanism 928, and a flow module 930 having a respiratory connector in the form of mouthpiece 932. The subject 934 is shown exercising on treadmill belt 936, having treadmill controller 938 supporting the computing device 924. The mechanical support for the treadmill controller 942 is not shown in detail, and other treadmill components are omitted.

The arrowed jagged lines in FIG. 25 indicate communication links, such as wireless connections, between the components of the system. Various embodiments of the present invention can be used as the respiratory analyzer.

The wrist-mounted monitor may comprise a heart rate monitor, oximeter, or other physiological parameter monitor. The wrist mounted monitor may also have the functionality of a computing device, and may comprise a clock, processor, memory, display, data port, cable connections, barcode scanner, data entry mechanism (such as buttons, voice recognition system, stylus entry mechanism), wireless transceiver, communications link to a communications network, or other mechanisms. The wrist mounted monitor may have other functions, such as a telephone, chronometer, time display, stopwatch, GPS (global positioning system), or other feature.

The computing device may receive exercise parameters by data entry by the subject or other person (such as a trainer), scanning a barcode on exercise equipment, scanning a barcode within printed material accompanying exercise equipment, wireless transmission from exercise equipment or trainer, and the like. The computing device, for example a personal digital assistant (PDA), may comprise a processor, clock, memory, and software program executable on the processor.

The flow module includes a flow pathway through which the subject breathes, a flow meter providing a flow signal correlated with a flow rate of respired gases through the flow pathway, and a gas component sensor, in this example an oxygen sensor. The flow module can also include circuitry to function as a respiratory analyzer, or may operate in cooperation with one or more other devices to act as a respiratory analyzer, for example so as to determine metabolic rate, oxygen consumption, or some other parameter. A respiratory analyzer can be operable to determine.

The treadmill controller may communicate with one or more other devices, for example to indicate the start, end, duration, and intensity (e.g. treadmill speed and gradient) of physical activity.

A subject exercises while wearing a wrist-mounted monitor and/or torso-mounted activity monitor, and simultaneously breathing through the respiratory analyzer. Exercises of one or more intensity levels (for example at different treadmill belt speeds and gradients) can be performed.

As used here, the term exercise period may comprise an activity period, during which period the subject engages in physical activity, and a recovery period, during which time one or more of the person's physiological parameters substantially returns to a baseline level, corresponding to a resting level or other pre-exercise level.

A calibration function can be established between physiological parameters determined by the wrist-mounted monitor or torso mounted monitor and the physiological parameters provided by the respiratory analyzer. Hence, for example, a calibration function can be determined between heart rates determined by a wrist mounted heart rate monitor and metabolic rates determined by the respiratory analyzer.

D. Other Configurations

Other configurations are discussed below, including cardiac output determination, and use of activity monitors and physiological monitors.

Cardiac Output Determination

Respiratory analyzers according to embodiments of the present invention can be used in health improvement programs for cardiac patients and other recuperating subjects.

Oxygen consumption of a cardiac patient can be determined, and feedback provided to the subject patient based on the determined data. A health professional, such as a doctor, can accurately determine oxygen consumption by cardiac patients. The flow module, computation module, or other device in communication with them can communicate data to the health professional's personal computer for review. A cardiac rehabilitation program can be modified by the results, or the pace of a rehabilitation program correlated with determined oxygen consumption or cardiac output of the patients.

In other embodiments, a computation module receives data from a flow module so as to determine oxygen consumption ($VO_2$) and end tidal oxygen concentration, and further receives data corresponding to arterial hemoglobin oxygen saturation, for example from a pulse oximeter. As described in co-pending applications to Mault, such as WO00/67634 and corresponding applications, the contents of which are incorporated herein by reference, the computation module may then be adapted to determine cardiac output, as well as metabolic rate.

For example, cardiac output is given by the equation (from WO00/67634):

$$C.O.=VO_2/(CaO_2-CVO_2),$$

where $CaO_2$ is the oxygen content of arterial blood, $SaO_2$ is the oxygen saturation of arterial blood (%), and $PaO_2$ is the partial pressure of oxygen dissolved in arterial blood. Hence, as described in more detail in WO00/67634, cardiac output can be determined as follows. $VO_2$ is measured using a respiratory analyzer, such as an indirect calorimeter. The oxygen content of arterial blood is the sum of dissolved oxygen gas and the oxygen bound to hemoglobin, for example as given by an equation such as:

$$CaO_2=1.36(SaO_2)(Hgb)+0.0031(PaO_2)$$

where Hgb corresponds to the amount of hemoglobin in the blood. The amount of dissolved oxygen gas is very small compared with the amount of oxygen bound to hemoglobin. Hence, $CaO_2$ is determined from $SaO_2$, which can be conveniently determined with a pulse oximeter.

There is an analogous equation for venous blood: $CvO_2=1.36(SvO_2)(Hgb)+0.0031(PvO_2)$. Here, $PvO_2$, the partial pressure of oxygen in venous blood, is assumed to be the same as the end-tidal partial pressure of oxygen determined with a respiratory analyzer.

Further, $SvO_2$ can be found from $PvO_2$ using an oxyhemoglobin dissociation curve (which is sensitive to blood pH and to blood temperature). Hence, $CvO_2$ is found from the end-tidal oxygen measurement, using the oxyhemoglobin dissociation curve.

Hence, cardiac output can be determined using respiratory analyzers according to the present invention, adapted to determine $VO_2$ and end tidal oxygen concentration in exhalation, and further adapted to receive data from a pulse oximeter.

Cardiac output and metabolic rate can be monitored by a health professional over time, and the data used to provide improved rehabilitation programs. The physiological response to exercises of increased intensity can be used to provide feedback to the subject, for example by comparing the determined data with those of healthy and diseased individuals, or comparing the data with predetermined values (such as the boundaries of certain exercise regimes, maximum values, and the like).

Physiological Sensors

The flow module or computation module may also receive signals from one or more physiological sensors, such as a pulse oximeter, heart rate monitor, EKG, and the like, so as to monitor the health of the subject. Physiological sensors may also be used as activity monitors, as discussed below.

Activity Monitors

An activity monitor may comprise an accelerometer, pedometer, a global positioning system, or a physiological monitor providing a signal correlated with one or more physiological parameters, such body temperature, heart rate, a respiratory parameter (such as a respiratory volume or respiratory frequency), electrocardiograph (EKG) such as provided by the electrode. An activity monitor may be body-supported, such as torso-supported or wrist-mounted. Torso-mounted heart rate monitors are known in the exercise arts.

GPS (global positioning system) data can be used to determine a subject's speed, acceleration, and position, and this data can be correlated with the determined metabolic rate of the subject during the exercise. Embodiments of the present invention can be used by swimming, walking, running and cycling subjects. Activity monitors can be included within running shoes, as more fully described in U.S. Provisional App. 60/445,595.

Cycling

Respiratory analyzers according to the present invention can be used during other outdoor exercises such as cycling. Data can be stored within the flow module, the computation module, or another electronic device on the body of the person. The exercise equipment, such as cycle, can be provided with data receiving and recording equipment. For example, the flow module can communicate via a wireless connection with a computation module on a cycle. A global positioning system, or other device, can provide position, speed, acceleration, altitude, wind resistance, ambient temperature, ambient pressure, or other parameters for correlation with physiological parameters such as metabolic rate.

Medical Applications

Embodiments of the present invention are also useful for medical applications, such as diagnosing metabolic disorders, rehabilitation of cardiac patients, establishing the nutritional requirements of patients, and the like.

Exercise Use

Respiratory analyzers according to the present invention may be used in improved fitness programs. Improved methods of determining activity energy expenditure are also discussed below, including calibration of a physiological sensor.

Horses

Embodiments of the present invention can also be used in connection with other mammals, such as horses. In the case of a horse, the respiratory connector of a flow module is be configured to a horses mouth and nose. Horse masks are known in the art. Physiological parameters of the horse can be correlated with, for example, horse speed, as provided using a GPS system or other method, and used to improve training programs.

A horse rider may be provided with a headset so as to receive information regarding physiological parameters and other exercise parameters of the horse. In this embodiment, a flow module may be supported by the horse, and the computation module may supported by the horse or rider. Headwear worn by the rider may comprise functionalities of the computation modules described above. Headwear may comprise a voice synthesis system to provide audible renderings of equine data during the course of a horse ride. For example, a rider may hear "Metabolic rate (some determined value), horse speed (some determined value), heart rate (some determined value)" at intervals during a ride. Values may be absolute, in any convenient unit, or relative to predetermined values, such as previous maximums. The data can be transmitted from a flow module (or from other sensors, such as a horse heart rate sensor) to the headset by a wireless mechanism.

By comparing horse heart rate, metabolic rate, respiratory parameters, or other horse parameters with, for example, predetermined maximum values, feedback may be provided to the rider.

E. Exercise Use

Further discussion is provided regarding apparatus and methods related to exercise use, including an improved method of calibrating a physiological monitor or other activity sensor with an indirect calorimeter, and an improved method of determining activity energy expenditure for an activity.

Calibration of Physiological Sensor

The metabolic rate of a subject can be correlated with exercise intensity, as described more fully in U.S. Pat. No. 6,571,200 to Mault. Exercise intensity can be determined, for example using electrical signals provided by exercise equipment, speed (such as treadmill speed), gradient (such as treadmill gradient, or as determined from topographic or GPS data).

Activity data provided by a treadmill, other exercise machine, or an activity monitor can be converted to metabolic rate using a predetermined correlation between activity data and metabolic rate. The predetermined correlation can be established in controlled conditions, such as within a fitness center, or under typical conditions for a planned exercise program.

For example, a subject may wear a respiratory analyzer while walking. Data provided by the respiratory analyzer, such as metabolic rate, can be used to determine a correlation between activity energy expenditure (AEE) and signals provided by an activity monitor, such as a heart rate monitor or a pedometer.

A subject may wear a wrist-mounted heart monitor having a radio communication device, which is in communication with a computing device carried by the person. For example, a wrist-mounted device may communicate with a PDA. The calibration function may be stored in the memory of the PDA. In other embodiments data may be transmitted to a remote location, such as a remote server, for example over a communications network such as the Internet. As a subject exercises, the data provided by a heart rate monitor may be converted to caloric expenditure and a fat burning quantity.

Wireless communication between a respiratory analyzer and an activity monitor (such as a wrist-mounted physiological monitor), computation module, or other electronic device can be used to provide a display so as to allow a subject to monitor caloric expenditure during the course of an exercise. Encouraging feedback can also be provided to the person, as discussed in more detail elsewhere, for example in terms of energy expenditure in relation to some target, or in relation to previous activities.

The correlation between exercise intensity or activity monitor signal with metabolic rate can be then be used to determine calories expended during an exercise.

For example, a heart rate monitor can be conveniently worn by the subject, for example as a wrist-mounted monitor. Using a predetermined calibration function between heart rate and other physiological parameter (such as metabolic rate, respiratory quotient, fat burning rate, and the like), the other physiological parameter can be determined from a heart rate measurement. The calibration of a heart rate monitor allows a physiological parameter (other than heart rate) to be determined from a measured heart rate using a calibration function. The calibration function can be found by measuring the physiological parameter and heart rate simultaneously as a subject is at rest and/or exercises at one or more levels of exercise intensity. Exercise intensity may be speed (such as running speed or walking speed), repetition rate, or some other parameter.

Hence, a physiological parameter (such as metabolic rate) of a subject can be monitored using a heart rate monitor alone by providing a heart rate monitor to the subject having the calibration function stored in the memory of the heart rate monitor, determining a heart rate of the subject, and providing a software application program to determine the corresponding value of the physiological parameter using the calibration function and the determined heart rate.

A calibration function can also be used to relate an integrated heart rate over a time period, for example the total number of heart beats during the time period, with a physiological parameter such as the total metabolic expenditure during the time period. This calibration function can be determined using the system of FIG. 25, for example. The time period chosen may be an activity period, during which a physical activity is performed. The time period can also be chosen as an exercise period consisting of an activity period followed by a recovery period.

For example, a wrist-mounted heart rate monitor can be calibrated by determining a calibration function between heart rate and metabolic rate, the latter determined by the respiratory analyzer. A calibration function can be established between heart rate and other physiological parameters, such as respiratory parameters (oxygen consumption, carbon dioxide production, respiratory quotient, end tidal oxygen, end tidal carbon dioxide, concentration of other respiratory components such as acetone, other ketones, and the like), blood component concentration (such as blood lactate level or glucose level), cardiac output, EKG signal, body temperature, or other physiological parameter.

A calibration function can also be established between heart rate, such as determined by a wrist-mounted heart rate monitor, and an activity signal, correlated with a physical activity level of a subject. The activity signal can be provided an activity monitor (such as a torso-mounted activity monitor, for example using one or more accelerometers, a GPS (global positioning system) based monitor, exercise equipment, or the like, so that heart rate can be correlated with a physical activity level of the subject.

Metabolic rate can be determined by a metabolic rate meter such as a respiratory analyzer, one or more physiological parameters, either individually or in combination, such as body temperature, electrical signals from muscles, oxygen consumption in conjunction with heart rate or other parameter, or other physiological parameter, or estimated from signals provided by exercise equipment, or other methods known in the art.

During intense exercise the maximum oxygen consumption ($VO_2$(max)) and maximum heart rate can also be determined. Oxygen consumption and/or carbon dioxide production can be monitored after the end of an exercise, during a recovery period, as will be discussed in more detail later.

Resting energy expenditure (REE) can be determined from the resting metabolic rate measured with the subject at rest, and hence TEE (total energy expenditure), AEE (activity energy expenditure) and calorie balance can be determined. Diet log software provided by the computing device can be used to record foods consumed and hence caloric intake.

A subject may carry a computing device which receives physiological signals from a physiological monitor, stores the physiological signals in a memory of the computing device, and determines a caloric expenditure and fat burning by the person. Caloric expenditure can be determined by a first calibration function relating the physiological monitor and metabolic rate. Fat burning can be determined by a second calibration function relating the physiological signal and respiratory quotient.

For example, the physiological signal may be heart rate, heart rate and other physiological data, or some other data. The first and second calibration functions can be determined during a calibration session, for example by having a subject breathe through a respiratory analyzer while performing one or more exercises. During the calibration session, physiological signals may be stored in memory, and metabolic rate, oxygen consumption, or some other parameter or combination of parameters transmitted from the respiratory analyzer to the computing device. The physiological signals can be stored in memory, and caloric expenditure can be integrated over a time period. Caloric expenditure can be displayed to the subject by a display of the computing device. The display may also provide time, physical location, or other data to the person.

Activity Energy Expenditure Determination

Conventional methods of determining energy expenditure during exercise neglect the enhanced metabolic rate of a subject after the physical activity has ceased. An improved method of determining activity energy expenditure takes account of this recovery period.

An improved method of determining a metabolic energy expenditure of a subject due to a physical activity comprises determining the resting metabolic rate of the subject, then determining a total metabolic energy expenditure during an exercise recycle period (corresponding to an activity period during which the physical activity occurs, and a subsequent recovery period during which physiological parameters return to substantially pre-exercise levels). The activity energy expenditure of the subject due to the physical activity is calculated as the total metabolic energy expenditure minus the resting energy expenditure expected over the duration of the exercise recycle period (equal to the product of the resting metabolic rate and the duration of the exercise recycle period). The end of the recovery period can be determined as the time at which the metabolic rate of the subject returns to a level substantially equal to a baseline metabolic rate. The baseline metabolic rate may be the metabolic rate just prior to the start of the exercise, or the resting metabolic rate of the subject.

An improved metabolic rate meter for exercise use comprises a metabolic rate meter, which provides a metabolic rate of the subject, a memory capable of storing a resting metabolic rate of the subject, a processor, a clock; and a software application program. The program can be adapted to determine the start time of a physical activity (for example, by receiving a signal from the subject, a signal from exercise equipment, providing an alert so as to cause the subject to start a physical activity, and the like), determine the end time of the physical activity (optional, for example by methods discussed in relation to start time determination), and to determine a recovery period of the subject (the time at which the subject is substantially in a resting state after completing an exercise). The software is also adapted to determine an activity energy expenditure over the exercise recycle period, accounting for the recovery period.

The end of the recovery period can be determined as the time when the metabolic rate of the subject become substantially equal to a baseline level, such as the resting metabolic rate or the metabolic rate of the subject just before the onset of the physical activity. The recovery period can also be determined as the time at which one or more physiological parameters (such as heart rate) become substantially equal to a baseline level, such as resting levels or levels existing at the onset of the exercise.

The activity energy expenditure corresponding to a particular exercise can be stored in a memory of the metabolic rate meter, or other electronic device. For example, the AEE for the exercise may be stored in a PDA an used in an calorie balance program, diet log, or the like. In an improved health-related program, a subject uses the determined AEE to determine a calorie balance, instead of general formulas and tables which may not be accurate for the subject.

Calibration of Physiological Sensor Including Recovery Time Effects

Metabolic rate meters, such as indirect calorimeters, may be inconvenient to use during routine exercises. It is more convenient to the subject to calibrate a less cumbersome activity monitor (such as a heart rate monitor) with an accurate metabolic rate meter (such as an indirect calorimeter). In the example below, the less cumbersome activity monitor is a heart rate monitor. However, other activity monitors can be used.

As discussed above, a subject's metabolic rate remains at a higher level after a physical activity has ended. Metabolic rate may fall to the subject's resting metabolic rate during a recovery period.

As is known in the exercise art, exercise recovery can be approximated by a fast recovery process (which may be complete within minutes), and a slow recovery process (which may require hours to complete). After light or moderate exercise, the slow recovery process may be neglected. After more intense exercise, the slow recovery process may be characterized by direct measurements. The characteristics of the slow recovery process (such as recovery time) may also be estimated from initial measurements, or approximated using an algorithm including for example, the exercise intensity, fast recovery time measurements, and the degree of heart rate elevation remaining relative to a resting state after the fast recovery process is complete.

The fast and slow recovery processes may be characterized linear declines of heart rate and metabolic rate to baseline levels, having fast and slow recovery times respectively. Alternatively, other mathematical functions such as exponentials, logs, power series, and the like may be used.

An improved method of calibrating a heart rate monitor allows a subject to more accurately determine metabolic energy expenditure using a heart rate monitor by accounting for the enhanced metabolic rate during a recovery period.

The subject performs a physical activity during an activity period. The activity period may be a fixed time, include a certain number of repetitions, include warm up period, or other factors. After the activity is completed, the subject enters a recovery period. The recovery period is a period during which a person's metabolic processes return to substantially a resting state.

In practice, the physiological recovery period may be quite long, so a recovery period may be chosen which is less than that for full physiological recovery from the exercise. The recovery period may be measured as the time until heart rate, metabolic energy expenditure, or some other physiological parameter returns to substantially pre-activity levels. The monitoring may stop, for example, when the physiological parameter is within 5, 10, 20, 30, 40, or 50% (or greater or intermediate levels) of the baseline level, or after the last recovery process is complete, and a correction factor applied for the non-monitored period.

The heart rate of the subject is monitored during the exercise recycle period, consisting of the activity period and the subsequent recovery period. A cumulative excess heart rate can be determined for the subject during the exercise recycle period, which is the total number of heart beats in excess of the those which would arise from the resting heart beat over the corresponding time period. This cumulative excess heart rate can be correlated with the activity energy expenditure (AEE) for the physical activity and subsequent recovery period.

Metabolic energy expenditure is determined for the subject over the exercise recycle period, and an excess metabolic expenditure is determined for the subject over this period. The excess metabolic expenditure is the energy expended by the subject over the activity period and recovery period in excess of that which would have been expended if the physical activity had not taken place. If the subject starts from a resting state, the excess metabolic expenditure will be the activity energy expenditure (AEE). Generally, total energy expenditure (TEE) is the sum of resting energy expenditure (REE) and activity energy expenditure (AEE).

The excess metabolic expenditure is correlated with the excess heart beats. This correlation may be repeated one or more times, for example at different activity intensity levels.

A calibration function is then determined between the heart rate (or excess cumulative heart rate) and the metabolic expenditure (or excess energy expenditure) of the subject over the exercise recycle time (the activity period and the subsequent recovery period). The calibration function can relate to the relationship between total values (such as between total heart beats and total energy expenditure), between excess values (such as between the excess heart beats in addition to the resting heart rate and excess energy expenditure over the resting metabolic rate or other baseline level), between total and excess values, or between other values as will be clear to those skilled in the art.

Figure 26:
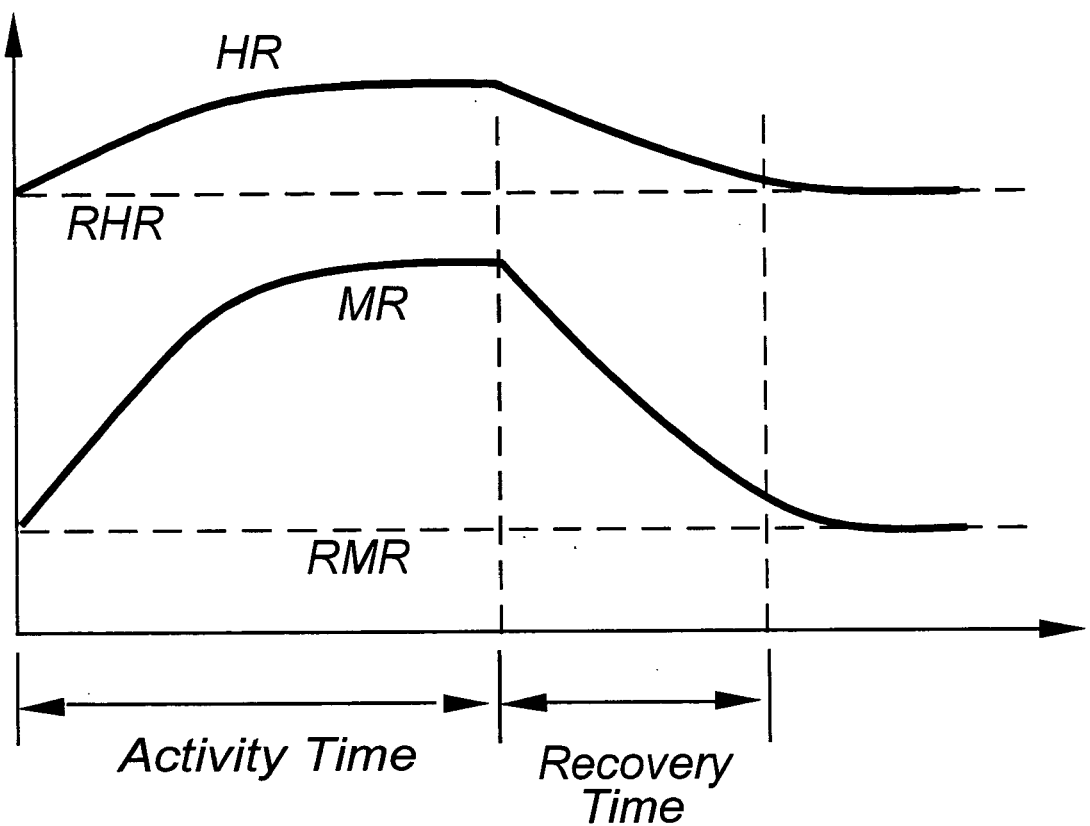
FIG. 26 is a graph illustrating heart rate measurements during a period of rest, and during a metabolic rate measurement period.

For example, FIG. 26 shows a graph illustrating a possible behavior of heart rate (HR) and metabolic rate (MR) over an exercise recycle time, comprising an activity period and a subsequent recovery period. The resting metabolic rate (RMR) and resting heart rate (RHR) are also shown. The areas under the curves minus the baseline can be compared so as to determine a calibration function between heart beats above a baseline level and an activity energy expenditure.

During future exercises, a subject measures heart rate during and after a physical activity. The number of heart beats in excess of a resting level over a corresponding time period can be determined, and the energy expenditure determined using a calibration function relating e.g. excess heart beats due to a physical activity and activity energy expenditure.

Exercise Intensity Effects

Exercise intensity can be determined by speed (such as treadmill speed, running speed, cycle speed, and speed equivalents, such as the speed corresponding to e.g. wheel rotation of a stationary exercise cycle), gradient (e.g. of a treadmill), acceleration, resistance, physical location (for example as provide by a global positioning system), altitude, electrical signals provided by exercise equipment, one or more physiological parameters (such as heart rate), or some combination, integration, rate of change, summation, multiplication, or other determination based on one or more of the above or similar parameters.

During a medium level of activity, the instantaneous oxygen consumption may not be well correlated with metabolic rate, due to lactate metabolism and other anaerobic processes. The caloric expenditure of the exercise can be determined from the total excess oxygen consumption above a baseline, substantially the resting oxygen consumption, if oxygen consumption is also determined during the recovery period. This may be calibrated against the total excess heart rate integrated above a baseline corresponding substantially to resting heart rate.

After calibration, the system may be used by wearing the belt-mounted and/or torso-mounted activity monitors. Heart rate may be converted to metabolic rate and hence used to calculate resting energy expenditure as will be described in more detail later.

For medium levels of exercise, the heart rate can be correlated with energy expenditure using one or more measured physiological parameters, and a calibration function in the form of a lookup table, numerical model, or other calculation. Excess heart rate, above a resting baseline, can be integrated and used to calculate activity energy expenditure (AEE).

Exercise equipment can be provided having an output correlated with the intensity of exercise. For example, an improved treadmill may comprise the provision of data such as speed and gradient of treadmill, personal identification entered into the treadmill, RMR, RQ, VEQ, and other respiratory parameters provided by the subject, for example in the form of a calibration function, and heart rate measurements.

For example, a heart rate or heart meter may be provided in the handles of exercise equipment, or a wrist-mounted or torso-mounted activity monitor may transmit heart rate information to the exercise equipment.

The calibration function between heart rate and respiratory parameters may be stored in the form of a data table, numerical relationship, or other mathematical form. The calibration function may be stored on a personal computing device carried by the subject, within the exercise equipment, within the heart rate monitor carried by the person, or elsewhere.

Respiratory Quotient

The respiratory quotient, as determined by the respiratory analyzer, can be used to determine the onset of anaerobic exercise. A calibration function relating heart rate and respiratory quotient can be determined, so as to allow a heart rate monitor to provide an estimation of respiratory quotient. The calibrated heart rate monitor can then be used to determine the onset of anaerobic exercise.

Heart rate may be correlated with respiratory quotient using a calibration function. Hence, when heart rate reaches a level at which anaerobic metabolism is expected, a colored light, audible signal, or other alert can be provided to the person. This allows a subject to exercise either exclusively in anaerobic regime, or in proximity to the anaerobic-aerobic threshold.

The display of a calibrated device can be used to show a fat burning quantity to the person. The fat burning quantity is determined by a total energy expenditure and values of respiratory quotient over the corresponding time period.

A calibration function can also be determined between heart rate and presence of respiratory components in the breath indicative of fat burning, such as ketones, aldehydes, or other volatile organic compounds.

F. Improved Methods of Determining Resting Metabolic Rate (RMR)

An improved method of determining RMR, and an improved heart rate monitor which can be used in RMR determinations, are described below.

A metabolic rate meter, such as an indirect calorimeter, is used to determine the metabolic rate of a subject. If the subject is fully relaxed, the determined metabolic rate is the resting metabolic rate (RMR) of the person. However, it can be difficult for a subject to fully relax under measurement conditions, such as an office or medical setting. A subject may relax more easily at home. However, the technical nature of metabolic rate measurements may require the subject to be in an office location. Also, a subject may find it difficult to relax under the measurement protocol, such as breathing through a mouthpiece. However, a resting heart rate can be determined by providing the subject with a heart rate monitor, which may be taken home by the subject for use when the subject is relaxed.

In an improved method of determining RMR for a subject, a measured metabolic rate is determined during a measurement period. A measurement period heart rate is also determined during the measurement period. For example, the subject may breath through an indirect calorimeter while wearing a heart rate monitor. The measurement period heart rate may be determined as an average heart rate during the measurement period. The measurement period is the period of time over which the measured metabolic rate is determined. The subject may breath through an indirect calorimeter for a longer period of time, during which some data may be discarded.

The resting metabolic rate (RMR) of the subject is then determined from the resting heart rate, the measurement period heart rate, and the measured metabolic rate.

For example, if RHR is the resting heart rate, MHR is the heart rate during the measurement period, MR is the measured metabolic rate, and RMR is the resting metabolic rate, then RMR can be calculated as: $RMR = (RHR/MHR)MR$.

This implicitly assumes metabolic rate is proportional to heart rate. Other equations can be used, as will be clear to those skilled in the art. For example, the ratio of RHR to MHR, or the individual terms, may be adjusted by a correction term, for example scaled by a power coefficient or multiplied by a numerical coefficient. Such correction terms can be determined for the individual or for demographic groups.

The resting heart rate can be determined providing a subject with a heart rate monitor and measuring heart rate over a time period, during at least part of which the subject is relaxed. Heart rate can be readily be monitored over the time period (for example minutes, hours, or one or more days). The determined time-dependent heart rate can be analyzed so as to determine the heart rate of the subject when relaxed. For example, a subject may press a button on a heart rate monitor so as to start monitoring when the subject is relaxed. Alternatively, a period during which average heart rate was at its lowest can be identified. Periods of anomalously low heart rate, for example due to hormonal action, may be avoided, for example by recording drug use, meals, health conditions, and the like.

A measurement heart rate is determined during the measurement of metabolic rate of the subject. The measurement heart rate may be the average heart rate of the subject during the time that the metabolic rate is determined. The measurement heart rate is then compared with the resting heart rate determined for the subject, at some other convenient time when the subject was fully relaxed. The determined metabolic rate can then be scaled by the ratio of measurement heart rate to resting heart rate to allow resting metabolic rate to be determined.

The subject is provided with a heart rate monitor, such as a wrist-mounted heart rate monitor. The subject's heart rate is monitored over a period of time. The period of time may one or more hours, days, weeks, or months, chosen so as to include a period of relaxation. Relaxation of the subject is facilitated by only requiring the use the heart rate monitor, which can be relatively unobtrusive. The resting heart rate of the subject is determining from the monitored heart rate of the subject during the period of heart rate monitoring. For example, the resting heart rate may be the lowest heart rate during the period of time, for example as measured over a continuous period of one or more minutes. For example, the resting heart rate may be as the lowest value of heart rate averaged over a certain period (such as one, five, ten or more minutes, or one or more hours).

The subject may also press a button on a heart rate monitor when they are relaxing or intend to relax, so as to start a period of time during which resting heart rate is established. For example, the subject may press a button or otherwise initiate resting heart rate determination at the start of a period of time during which they intend to relax, then press another button, or the same button again, or otherwise terminate the resting heart rate determination after they conclude the period of relaxation.

Figure 27:
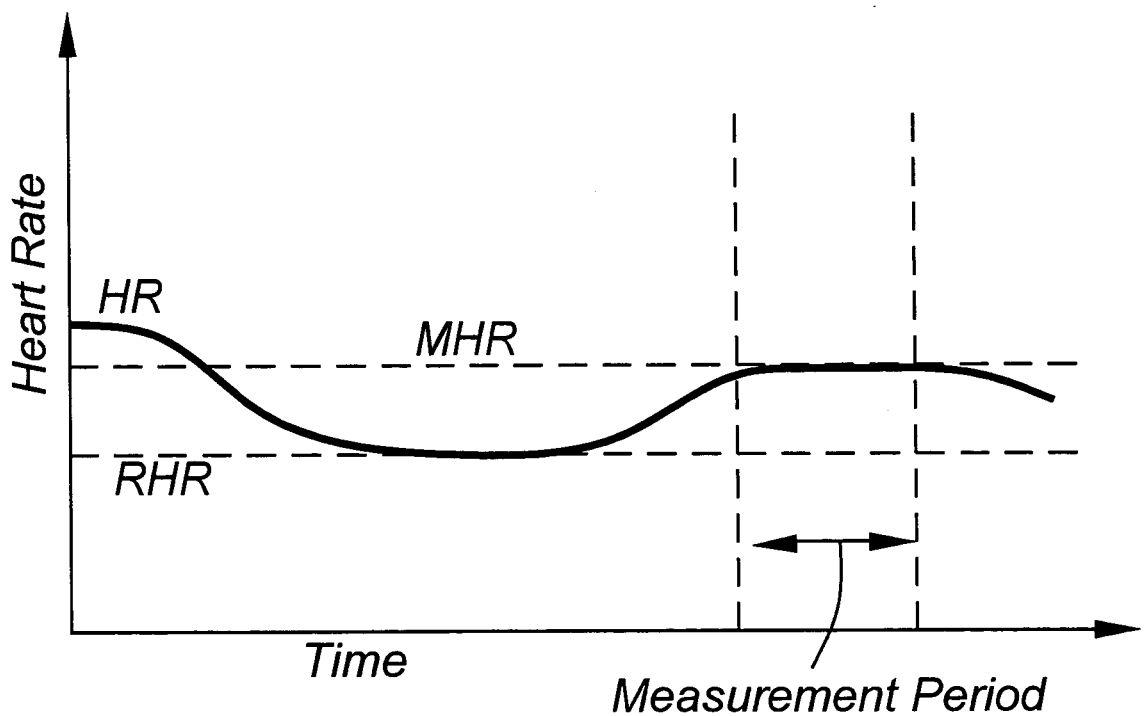
FIG. 27 shows a graph illustrating a possible behavior of heart rate (HR) and metabolic rate (MR) over an exercise recycle time (activity time followed by recovery time).

FIG. 27 illustrates a graph showing heart rate (HR) of a subject versus time. The subject is provided with a heart rate monitor at the initial time (or earlier). Resting heart rate is determined as the lowest level of heart rate during the subsequent time. During the measurement period, the person's metabolic rate (MR) and measurement period heart rate (MHR) are determined, for example as the average heart rate during the time when metabolic rate is measured. The person's resting metabolic rate RMR can be determined as MR scaled by the ratio of MHR to RHR.

Heart Rate Monitor

An improved heart rate monitor, comprises a sensor adapted to respond to a beating of a subject's heart, such as a pulse sensor, a processor, a memory, a clock, and a display. A software application program, executed by the processor, is adapted to calculate a heart rate of the subject at intervals and present a visual representation of the heart rate on the display of the heart rate monitor, for example in the form of a number. The program further is operable to determine a resting heart rate of the subject. For example, the monitor may determine heart rate on a minute-by-minute basis, and determine the lowest value, or some lowest average value. For example, the lowest heart rate over a 1, 2, 3, 4, 5, 10, 15, 20, or some other number of minutes may be determined.

The monitor may also be operable to determine a measurement heart rate during a measurement period during which a metabolic rate of the subject is determined. For example, the monitor may be in wireless communication with an indirect calorimeter through which the subject breathes.

The monitor may also communicate with the metabolic rate meter so as to allow an accurate determination of the resting metabolic rate of the subject. For example, a heart rate monitor may be in two way communication with an indirect calorimeter.

An improved heart rate monitor comprises a sensor adapted to provide a signal in response to heart beats, a controller, a memory; a clock, and an algorithm executed by the controller, adapted to measure a heart rate over a period of time and to determine a metabolic energy expenditure of the subject over the period of time using a calibration function. The calibration function is determined by measuring the metabolic energy expenditure of the subject during an activity period and a recovery period, and comparing the metabolic energy expenditure with the heart rate of the subject over a corresponding time period.

G. Other Embodiments

Embodiments of the present invention may be used in other flow monitoring applications, such as medical ventilators, breathing masks, industrial process monitoring, and the like.

Examples provided are intended to be illustrative, and not limiting. Other embodiments will be clear to those skilled in the relevant arts. Elements of provided examples can be combined in different ways, or modified, as will be clear to those skilled in the relevant arts. Alternatives, features, and other aspects presented in relation to illustrative embodiments of the present invention may also be used in other embodiments of the invention, as will be clear to those skilled in the relevant arts. Other embodiments will be clear to those skilled in the relevant arts.

What is claimed is:

1. A respiratory analyzer for determining a respiratory parameter of a subject, comprising:
   a respiratory connector, through which the subject breathes;
   a filter module, in fluid communication with the respiratory connector, through which respired gases pass as a subject breathes through the respiratory analyzer, the filter module including a pathogen filter;
   a flow tube, enclosing a central flow pathway, the flow tube having a first end and a second end, a first end portion proximate to the first end, and a second end portion proximate to the second end;
   a chamber, in fluid communication with the filter module, surrounding the first end portion of the flow tube, the chamber and the central flow pathway being in fluid communication through one or more apertures in the first end portion of the flow tube;
   a wind guard connected to an external surface of flow tube and having a flared portion extending beyond the second end of the flow tube, wherein the wind guard encloses an atmospheric chamber surrounding the second end portion of the flow tube, the atmospheric chamber opening to the atmosphere through an atmospheric aperture bounded by the wind guard and having a diameter greater than the external diameter of the flow tube, the atmospheric chamber and the central flow pathway being in fluid communication through one or more apertures in the second end portion of the flow tube;
   a gas sensor, providing a gas sensor signal responsive to a partial pressure of a predetermined gas within the central flow pathway;
   a flow meter, providing a flow meter signal correlated with a flow rate of gases within the central flow pathway; and
   a computation module, receiving the flow meter signal and the gas sensor signal, and operable to compute the respiratory parameter of the subject.

2. The respiratory analyzer of claim 1, wherein the first end portion of the flow tube includes a plurality of apertures providing a plurality of gaseous paths between the central flow pathway and the chamber.

3. The respiratory analyzer of claim 1, wherein the second end portion of the flow tube includes a plurality of apertures providing a plurality of gaseous paths between the central flow pathway and the atmospheric chamber.

4. The respiratory analyzer of claim 1, wherein the gas sensor is an oxygen sensor.

5. The respiratory analyzer of claim 1, wherein the flow meter includes a first ultrasonic transducer supported within the first end portion of the flow tube, and a second ultrasonic transducer supported within the second end portion of the flow tube, the first and second ultrasonic transducers being in ultrasonic communication through gases within the central flow pathway.

6. The respiratory analyzer of claim 1, wherein the subject breathes through a flow module supported by the head of the subject, the computation module being a separate module supported by the body of the subject, the computation module being in electrical communication with the flow module through an electrical cable.

7. A respiratory analyzer for determining a respiratory parameter of a subject comprising:
   a) a flow module, the flow module including:
      a housing enclosing a flow pathway through which respired gases pass as the subject breathes through the respiratory analyzer;
      a flow meter, providing a flow signal correlated with a flow rate of gases through a portion of the flow pathway, wherein the flow pathway includes a flow tube partially enclosing a central flow pathway, the flow tube having a first end and a second end, a first end portion proximate to the first end, and a second end portion proximate to the second end;
      a gas sensor, providing a gas sensor signal correlated with a partial pressure of a predetermined gas within the flow pathway, wherein the gas sensor is an oxygen sensor, and the respiratory parameter is a consumed oxygen volume;
   b) a computation module, the computation module being in data communication with the flow module, and operable to determine a respiratory parameter of the subject, wherein the flow module is adapted to be supported by a strap disposed around the head of the subject, the computation module is adapted to be supported on the torso of the subject, and the flow module and the computation module are in electrical communication through a cable;
   c) mouthpiece through which the subject breathes;
   d) filter module including a pathogen filter operable to remove a pathogen from subject's exhalations passing through the respiratory analyzer as the subject breathes through the respiratory analyzer;
   e) a chamber disposed so as to substantially surround the first end portion of the flow tube;
   f) a first plurality of apertures disposed in the first end portion of the flow tube, through which the chamber is in fluid communication with the central flow pathway;
   g) a wind guard disposed around the second end portion of the flow pathway, operable to partially shield the second end portion of the flow pathway from external air movements, an interior surface of the wind guard defining an atmospheric chamber substantially surrounding the second end portion of the flow tube, the atmospheric chamber being in fluid communication with the atmosphere through an atmospheric aperture; and h) a second plurality of apertures in the second end portion of the flow tube, through which the central flow pathway is in fluid communication with the atmospheric chamber.

8. The respiratory analyzer of claim 7, wherein the atmospheric aperture has a diameter greater than an external diameter of the flow tube.

9. The respiratory analyzer of claim 7, wherein the second plurality of apertures includes a plurality of aperture rings encircling the second end of the flow tube, each aperture ring including at least ten apertures.

10. A respiratory analyzer for determining a respiratory parameter of a subject, comprising:
 a respiratory connector, through which the subject breathes;
 a flow module housing;
 a flow tube within the flow module housing, partially enclosing a central flow pathway through which respired gases from the subject flow when the subject breathes through the respiratory analyzer, the flow tube having a first end and a second end;
 a first ultrasonic transducer supported proximate to the first end of the flow tube;
 a second ultrasonic transducer supported proximate to the second end of the flow tube, wherein the first and second ultrasonic transducers are operable to communicate ultrasonic signals through gases in the central flow pathway, and to provide flow rate signals correlated with a flow rate of gases in the central flow pathway;
 an oxygen sensor providing an oxygen sensor signal correlated with a partial pressure of oxygen in the central flow pathway; and
 a computation module, operable to determine the respiratory parameter of the subject, wherein the central flow pathway is in fluid communication with the respiratory connector through a first plurality of apertures disposed in proximity to the first end of the flow tube, and the central flow pathway is in fluid communication with atmospheric gas through a second plurality of apertures disposed in proximity to the second end of the flow tube.

11. The respiratory analyzer of claim 10, wherein a chamber surrounds a first end portion of the flow tube proximate to the first end of the flow tube, wherein the chamber and the central flow pathway are in fluid communication through the first plurality of apertures.

12. The respiratory analyzer of claim 10, wherein an atmospheric chamber surrounds a second end portion of the flow tube proximate to the second end of the flow tube, wherein the central flow pathway and the atmospheric chamber are in fluid communication through the second plurality of apertures.

13. The respiratory analyzer of claim 10, wherein the atmospheric chamber is partially enclosed by a wind guard extending from the flow tube, the wind guard being operable to shield the second plurality of apertures from atmospheric air movements.

14. The respiratory analyzer of claim 10, wherein the respiratory parameter is an oxygen volume consumed by the subject.

15. The analyzer of claim 10, wherein the flow tube has a non-uniform cross-section having a minimum cross-sectional area at a position of minimum cross-section located between the first end of the flow tube and the second end of the flow tube.

\* \* \* \* \*